United States Patent
Forbes et al.

(10) Patent No.: US 12,233,168 B2
(45) Date of Patent: Feb. 25, 2025

(54) LOCALIZATION OF PAYLOAD DELIVERY SYSTEMS TO TUMOR SITES VIA BEACON CELL TARGETING

(71) Applicant: University of Massachusetts, Boston, MA (US)

(72) Inventors: Neil S. Forbes, Hadley, MA (US); Nele Van Dessel, Easthampton, MA (US); John Klier, Leverett, MA (US); Shane Taylor, Amherst, MA (US); Vishnu Raman, Amherst, MA (US)

(73) Assignee: University of Massachusetts, Boston, MA (US)

( * ) Notice: Subject to any disclaimer, the term of this patent is extended or adjusted under 35 U.S.C. 154(b) by 138 days.

(21) Appl. No.: 17/594,193

(22) PCT Filed: Apr. 8, 2020

(86) PCT No.: PCT/US2020/027302
§ 371 (c)(1),
(2) Date: Oct. 6, 2021

(87) PCT Pub. No.: WO2020/210378
PCT Pub. Date: Oct. 15, 2020

(65) Prior Publication Data
US 2022/0151947 A1    May 19, 2022

Related U.S. Application Data

(60) Provisional application No. 62/831,122, filed on Apr. 8, 2019.

(51) Int. Cl.
| A61K 9/51 | (2006.01) |
| A61K 47/68 | (2017.01) |
| A61K 47/69 | (2017.01) |
| B82Y 5/00 | (2011.01) |

(52) U.S. Cl.
CPC ........ *A61K 9/5169* (2013.01); *A61K 47/6835* (2017.08); *A61K 47/6935* (2017.08); *B82Y 5/00* (2013.01)

(58) Field of Classification Search
CPC .............. A61K 47/6835; A61K 47/68; A61K 39/0275; B82Y 5/00
See application file for complete search history.

(56) References Cited

U.S. PATENT DOCUMENTS

| 6,677,153 B2 | 1/2004 | Iversen |
| 9,867,785 B2 | 1/2018 | Brahmbhatt et al. |
| 10,808,014 B2 | 10/2020 | Steidler et al. |
| 2009/0175829 A1 | 7/2009 | Forbes et al. |
| 2009/0208534 A1 | 8/2009 | Xu et al. |
| 2011/0293705 A1 | 12/2011 | Irvine et al. |
| 2015/0306238 A1 | 10/2015 | Baker et al. |
| 2015/0320694 A1 | 11/2015 | Gu et al. |
| 2017/0035837 A1 | 2/2017 | Mccormick et al. |
| 2017/0333490 A1 | 11/2017 | Forbes et al. |
| 2018/0008682 A1 | 1/2018 | Zhao et al. |
| 2018/0140710 A1 | 5/2018 | Thayumanavan et al. |
| 2019/0030185 A1 | 1/2019 | Mirkin et al. |
| 2024/0115671 A1 | 4/2024 | Forbes et al. |

FOREIGN PATENT DOCUMENTS

| CA | 2979760 A1 * | 9/2016 | ............. A61K 35/74 |
| JP | 2024511230 | 3/2024 | |
| WO | WO-2006091483 A1 | 8/2006 | |
| WO | WO-2016176164 A1 | 11/2016 | |
| WO | WO-2020014543 A2 | 1/2020 | |
| WO | WO-2020210378 A1 | 10/2020 | |
| WO | WO-2022174224 A2 | 8/2022 | |
| WO | WO-2022174226 A1 | 8/2022 | |
| WO | WO-2022174227 A2 | 8/2022 | |
| WO | WO-2022174224 A3 | 9/2022 | |
| WO | WO-2022174227 A3 | 9/2022 | |

OTHER PUBLICATIONS

"European Application Serial No. 20787821.6, Response Filed Jun. 14, 2022 to Communication Pursuant to Rules 161 (2) and 162 EPC mailed Dec. 9, 2021.", 9 pgs.
"International Application Serial No. PCT/US2020/027302, International Preliminary Report on Patentability mailed Oct. 21, 2021", 9 pgs.
"International Application Serial No. PCT/US2022/070578, International Search Report mailed Aug. 3, 2022", 5 pgs.
"International Application Serial No. PCT/US2022/070578, Invitation to Pay Additional Fees mailed May 24, 2022", 2 pgs.
"International Application Serial No. PCT/US2022/070578, Written Opinion mailed Aug. 3, 2022", 6 pgs.
"International Application Serial No. PCT/US2022/070582, International Search Report mailed Jun. 6, 2022", 3 pgs.
"International Application Serial No. PCT/US2022/070582, Written Opinion mailed Jun. 6, 2022", 7 pgs.
"International Application Serial No. PCT/US2022/070583, International Search Report mailed Jul. 25, 2022", 5 pgs.
"International Application Serial No. PCT/US2022/070583, Invitation to Pay Additional Fees mailed May 6, 2022", 2 pgs.
"International Application Serial No. PCT/US2022/070583, Written Opinion mailed Jul. 25, 2022", 9 pgs.
Bierschenk, D., et al., "The *Salmonella* pathogenicity island-2 subverts human NLRP3 and NLRC4 inflammasome responses.", J Leukoc Biol, 2019. 105(2), (2019), 10 pgs.
Au, J.L., et al., "Delivery of cancer therapeutics to extracellular and intracellular targets: Determinants, barriers, challenges and opportunities", Adv Drug Deliv Rev, 2016. 97, (2016), 53 pgs.
(Continued)

*Primary Examiner* — James W Rogers
(74) *Attorney, Agent, or Firm* — Schwegman Lundberg & Woessner, P.A.

(57) ABSTRACT

Provided herein are compositions comprising nanoparticles, wherein the nanoparticles comprise at least one payload, wherein the nanoparticles further comprise at least one surface bound functional group and method of their use.

17 Claims, 9 Drawing Sheets

(56) References Cited

OTHER PUBLICATIONS

Benoun, J.M, et al., "Optimal protection against *Salmonella* infection requires noncirculating memory", Proc Natl Acad Sci U S A, 2018. 115(41, (2018), 7 pgs.
Beuzon, C.R, et al., "*Salmonella* maintains the integrity of its intracellular vacuole through the action of SifA", EMBO J 19, (2000), 15 pgs.
Brawn, L.C., "*Salmonella* SPI1 effector SipA persists after entry and cooperates with a SPI2 effector to regulate phagosome maturation and intracellular replication", Cell Host Microbe, 2007. 1(1), (2007).
Camacho, E.M., et al., "Engineering *Salmonella* as intracellular factory for effective killing of tumour cells", Sci Rep, 2016. 6, (2016), 12 pgs.
Chakravortty, D., "*Salmonella* pathogenicity island 2 mediates protection of intracellular *Salmonella* from reactive nitrogen intermediates", J Exp Med, 2002. 195(9), (2002), 12 pgs.
Chatterjee, J, et al., "Development of a peptide that selectively activates protein phosphatase-1 in living cells", Angewandte Chemie (International ed 51, (2012), pp. 10054-10059.
Choi, J., et al., "*Salmonella* pathogenicity island 2 expression negatively controlled by EIIA<NtrSsrB interaction is required for *Salmonella* virulence", Proceedings of the National Academy of Sciences, 2010. 107(47), (2010), 6 pgs.
Chong, A., et al., "A role for the *Salmonella* Type III Secretion System 1 in bacterial adaptation to the cytosol of epithelial cells", Mol Microbiol, 2019. 112(4), (2019), 27 pgs.
Critchley, R.J., et al., "Potential therapeutic applications of recombinant, invasive *E. coli*", Gene Ther, 2004. 11(15), (2004), 11 pgs.
Critchley-Thorne, R.J., "Recombinant *Escherichia coli* expressing invasin targets the Peyer's patches: the basis for a bacterial formulation for oral vaccination", Mol Ther, 2006. 14(2), (2006), 9 pgs.
Dougan, G., "*Salmonella enterica* serovar Typhi and the pathogenesis of typhoid fever", Annu Rev Microbiol, 2014. 68, (2014), 22 pgs.
Duong, M, et al., "Bacteria-cancer interactions: bacteria-based cancer therapy", 1-2 Experimental & Molecular Medicine Web, (2019), 2 pgs.
Eisele, N.A., et al., "*Salmonella* require the fatty acid regulator PPARdelta for the establishment of a metabolic environment essential for long-term persistence.", Cell Host Microbe 14, (2013), 171-182.
Eswarappa, S.M., et al., "Division of the *Salmonella*-containing vacuole and depletion of acidic lysosomes in *Salmonella*-infected host cells are novel strategies of *Salmonella enterica* to avoid lysosomes.", Infect Immun, 2010. 78(1), (2010), 12 pgs.
Finn, C.E., et al., "A second wave of *Salmonella* T3SS1 activity prolongs the lifespan of infected epithelial cells", PLoS Pathog, 2017. 13(4), (2017), 28 pgs.
Forbes, N.S, "Engineering the perfect (bacterial) cancer therapy", Nature Reviews Cancer 10, (2010), 24 pgs.
Forbes, N.S, "Sparse initial entrapment of systemically injected *Salmonella typhimurium* leads to heterogeneous accumulation within tumors", Cancer Res 63, (2003), pp. 5188-5193.
Franchi, L., et al., "Cytosolic flagellin requires Ipaf for activation of caspase-1 and interleukin 1beta in *Salmonella*-infected macrophages", Nat Immunol, 2006. 7(6), (2006), 8 pgs.
Freeman, "The *Salmonella* enterica Serovar Typhimurium Translocated Effectors SseJ and SifB Are Targeted to the *Salmonella*-Containing Vacuole", Infect Immun., (Jan. 7, 2003), 10 pgs.
Galan, J.E., "*Salmonella* interactions with host cells: type III secretion at work.", Annu Rev Cell Dev Biol 17, (2001), pp. 53-86.
Ganai, S., "In tumors *Salmonella* migrate away from vasculature toward the transition zone and induce apoptosis", Cancer Gene Ther 18, (2011), pp. 457-466.
Gaudet, R.G., et al., "Innate Recognition of Intracellular Bacterial Growth Is Driven by the TIFA-Dependent Cytosolic Surveillance Pathway", Cell Rep, 2017. 19(7), (2017), 14 pgs.
Gauger, E.J., et al., "Role of motility and the flhDC Operon in *Escherichia coli* MG1655 colonization of the mouse intestine", Infect Immun, 2007. 75(7), (2007), 10 pgs.
Guo, H., et al., "Targeting tumor gene by shRNA-expressing *Salmonella*-mediated RNAi", Gene Ther, 2011. 18(1), (2011), 1 pg.
Hallstrom, K., "*Salmonella* Interaction with and Passage through the Intestinal Mucosa: Through the Lens of the Organism", Front Microbiol, 2011. 2, (2011), 10 pgs.
Hanahan, Douglas, et al., "Hallmarks of Cancer: The Next Generation", Cell, vol. 144, Mar. 4, 2011, (Mar. 4, 2011), 646-674.
Higgins, D.E., "Delivery of protein to the cytosol of macrophages using *Escherichia coli* K-12", Mol Microbiol, 1999. 31(6), (1999), 11 pgs.
Hodak, H., "A *Salmonella typhi* homologue of bacteriophage muramidases controls typhoid toxin secretion", EMBO Rep, 2013. 14(1), (2013), 8 pgs.
Hu, X., et al., "Vi capsular polysaccharide: Synthesis, virulence, and application", Crit Rev Microbiol, 2017. 43(4), (2017).
Ibarra, J, et al., "Induction of *Salmonella* pathogenicity island 1 under different growth conditions can affect *Salmonella*-host cell interactions in vitro", Microbiology 156, (2010), pp. 1120-1133.
Ilyas, B., et al., "Regulatory Evolution Drives Evasion of Host Inflammasomes by *Salmonella typhimurium*", Cell Rep, 2018. 25(4), (2018), 14 pgs.
Knodler, L A, et al., "Dissemination of invasive *Salmonella* via bacterial-induced extrusion of mucosal epithelia", Proc Natl Acad Sci U S A 107, (2010), pp. 17733-17738.
Knuff, K., et al., "What the SIF Is Happening—The Role of Intracellular *Salmonella*-Induced Filaments", Front Cell Infect Microbiol 7, (2017), pp. 1-8.
Kong, W., "Utilizing *Salmonella* for antigen delivery: the aims and benefits of bacterial delivered vaccination", Expert Rev Vaccines 12, (2013), pp. 345-347.
Krieger, V, et al., "Reorganization of the endosomal system in *Salmonella*-infected cells: the ultrastructure of Salmonella-induced tubular compartments", PLoS Pathog 10, (2014), 24 pgs.
Kuhne, "RflM mediates target specificity of the RcsCDB phosphorelay system for transcriptional repression of flagellar synthesis in *Salmonella enterica*", Molecular Microbioloy., (Jun. 27, 2016), 16 pgs.
Leschner, S., et al., "Tumor invasion of *Salmonella enterica* serovar Typhimurium is accompanied by strong hemorrhage promoted by TNF-alpha", PLoS One, 2009. 4(8), (2009), 11 pgs.
Li, Z., et al., "Pyroptosis of *Salmonella typhimurium*-infected macrophages was suppressed and elimination of intracellular bacteria from macrophages was promoted by blocking", QseC. Sci Rep, 2016. 6, (2016), 12 pgs.
Liss, V, et al., "*Salmonella enterica* Remodels the Host Cell Endosomal System for Efficient Intravacuolar Nutrition", Cell Host Microbe 21, (2017), pp. 390-402.
Liu, T., et al., "NF-kappaB signaling in inflammation", Signal Transduct Target Ther, 2017. 2, (2017), 9 pgs.
Low, K.B, "Lipid A mutant *Salmonella* with suppressed virulence and TNFalpha induction retain tumor-targeting in vivo", Nature biotechnology 17, (1999), pp. 37-41.
Macnab, R.M., "Genetics and biogenesis of bacterial flagella", Annu Rev Genet, 1992. 26, (1992).
Morrissey, D., "Targeting with Systemically Administered Bacteria", Current Gene Therapy 10, (2010), 12 pgs.
Mosberg, J.A, "Lambda red recombineering in *Escherichia coli* occurs through a fully single-stranded intermediate", Genetics, (2010), 21 pgs.
Mosberg, J.A., et al., "Improving lambda red genome engineering in *Escherichia coli* via rational removal of endogenous nucleases", PLoS One, 2012. 7(9), (2012), 12 pgs.
Mosberg, J.A., "Lambda red recombineering in *Escherichia coli* occurs through a fully single-stranded intermediate", Genetics, 2010. 186(3), (2010), 20 pgs.
Nakayama, K., "Construction of an ASD+ expression-cloning vector-stable maintenance and high-level expression of cloned genes in a *Salmonella* vaccine strain", Bio-Technology, (1988), 6 pgs.
Nelson, R.H., "Signal Distortion: How Intracellular Pathogens Alter Host Cell Fate by Modulating NF-kappaB Dynamics", Front Immunol, 2018. 9, (2018), 10 pgs.
Parkhill, J., et al., "Complete genome sequence of a multiple drug resistant *Salmonella enterica* serovar Typhi CT18", Nature, 2001. 413(6858), (2001), 5 pgs.

(56) References Cited

OTHER PUBLICATIONS

Rahman, M.M, "Modulation of NF-kappaB signalling by microbial pathogens", Nat Rev Microbiol, 2011. 9(4), (2011), 16 pgs.

Rajashekar, R, et al., "Dynamic remodeling of the endosomal system during formation of Salmonella-induced filaments by intracellular *Salmonella enterica*", Traffic 9, (2008), pp. 2100-2116.

Raman, V, et al., "The motility regulator flhDC drives intracellular accumulation and tumor colonization of *Salmonella* ", Journal for Immunotherapy of Cancer. vol. 7, Issue 1, (Feb. 12, 2019), 16 pgs.

Raman, V., "The motility regulator flhDC drives intracellular accumulation and tumor colonization of *Salmonella* ", J Immunother Cancer 7, (2019), 16 pgs.

Ruiz-Albert, J, et al., "Complementary activities of SseJ and SifA regulate dynamics of the *Salmonella typhimurium* vacuolar membrane", Mol. Microbiol. 44, (2002), pp. 645-661.

Singer, H.M., ", RflM functions as a transcriptional repressor in the autogenous control of the *Salmonella flagellar* master operon flhDC", J Bacteriol, 2013. 195(18, (2013), 9 pgs.

Slee, E.A, "Executioner caspase-3, -6, and -7 perform distinct, non-redundant roles during the demolition phase of apoptosis", J Biol Chem 276, (2001), pp. 7320-7326.

Smith, C., et al., "Mapping the Regulatory Network for *Salmonella enterica* Serovar Typhimurium Invasion", MBio, 2016. 7(5), (2016), 14 pgs.

Spano, S., "Delivery of a *Salmonella typhi* exotoxin from a host intracellular compartment", Cell Host Microbe, 2008. 3(1), (2008), 9 pgs.

Stecher, B., et al., "Flagella and chemotaxis are required for efficient induction of *Salmonella enterica* serovar Typhimurium colitis in streptomycin-pretreated mice.", . Infect Immun, 2004. 72(7), (2004), 13 pgs.

Steele-Mortimer, O., "The *Salmonella*-containing vacuole: moving with the times", Curr Opin Microbiol, 2008. 11(1), (2008), 14 pgs.

Stritzker, J, et al., "Enterobacterial tumor colonization in mice depends on bacterial metabolism and macrophages but is independent of chemotaxis and motility", Int J Med Microbiol, 2010. 300(7):, (2010), 8 pgs.

Swofford, C.A, "Quorum-sensing *Salmonella* selectively trigger protein expression within tumors.", Proceedings of the National Academy of Sciences of the United States of America, (2015), 11 pgs.

Toley, B.J., "Motility is critical for effective distribution and accumulation of bacteria in tumor tissue", Integr Biol, (2012), 13 pgs.

Toley, B.J., "Motility is critical for effective distribution and accumulation of bacteria in tumor tissue.", Integr Biol, 2012. 4(2), (2012), 20 pgs.

Toso, J.F., et al., "Phase I study of the intravenous administration of attenuated *Salmonella typhimurium* to patients with metastatic melanoma", J Clin Oncol, 2002. 20(1, (2002), 19 pgs.

Vaidya, S., et al., "Substrate-induced conformational changes occur in all cleaved forms of caspase-6", J Mol Biol, (2011), 26 pgs.

Van Wijk, S.J.L, et al., "Linear ubiquitination of cytosolic *Salmonella typhimurium* activates NF-kappaB and restricts bacterial proliferation", Nat Microbiol, 2017. 2:, (2017), 1 pg.

Walsh, C.L., et al., "A multipurpose microfluidic device designed to mimic microenvironment gradients and develop targeted cancer therapeutics", Lab on a chip, (2009), 19 pgs.

Walsh, C.L., et al., "A multipurpose microfluidic device designed to mimic microenvironment gradients and develop targeted cancer therapeutics", Lab on a chip 9, (2009), pp. 545-554.

Walsh, C.L., et al., "A multipurpose microfluidic device designed to mimic microenvironment gradients and develop targeted cancer therapeutics", Lab on a chip, 2009. 9, (2009), 18 pgs.

Walsh, J.G, "Executioner caspase-3 and caspase-7 are functionally distinct proteases", Proc Natl Acad Sci U S A 105, (2008), pp. 12815-12819.

Wang, X., "IS5 inserts upstream of the master motility operon flhDC in a quasi-Lamarckian way", ISME J, 2011. 5(9), (2011), 9 pgs.

Winter, S.E., et al., "*Salmonella enterica* Serovar Typhi conceals the invasion-associated type three secretion system from the innate immune system by gene regulation", PLoS Pathog, 2014. 10(7), (2014), 16 pgs.

Winter, S.E., et al., "The *Salmonella enterica* serotype Typhi regulator TviA reduces interleukin-8 production in intestinal epithelial cells by repressing flagellin secretion", Cell Microbiol, 2008. 10(1), (2008), 15 pgs.

Winter, S.E., et al., "The TviA auxiliary protein renders the *Salmonella enterica* serotype Typhi RcsB regulon responsive to changes in osmolarity", Mol Microbiol, 2009. 74(1), (2009), 34 pgs.

Xu, Y., et al., "A Bacterial Effector Reveals the V-ATPase-ATG16L1 Axis that Initiates Xenophagy", Cell, 2019. 178(3), (2019), 36 pgs.

Yan, Y., et al., "Asd-based balanced-lethal system in attenuated Edwardsiella tarda to express a heterologous antigen for a multivalent bacterial vaccine", Fish Shellfish Immunol, (2013), 7 pgs.

Yang, N., et al., "Attenuated *Salmonella typhimurium* carrying shRNA-expressing vectors elicit RNA interference in murine bladder tumors", Acta Pharmacol Sin, 2011. 32(3, (2011), 7 pgs.

Yoon, S.I., et al., "Structural basis of TLR5-flagellin recognition and signaling", Science, 2012. 335(6070), (2012), 11 pgs.

Zeng, H., et al., "Flagellin is the major proinflammatory determinant of enteropathogenic *Salmonella*", . J Immunol, 2003. 171(7):, (2003), 8 pgs.

Zhang, K., et al., "Minimal SPI1-T3SS effector requirement for *Salmonella enterocyte* invasion and intracellular proliferation in vivo", PLoS Pathog 14, (2018), 30 pgs.

Zhang, M., "Trg-deficient *Salmonella* colonize quiescent tumor regions by exclusively penetrating or proliferating", J Control Release, 2015. 199, (2015), 25 pgs.

Zhao, M., et al., "Tumor-targeting bacterial therapy with amino acid auxotrophs of GFP-expressing *Salmonella typhimurium*", Proceedings of the National Academy of Sciences of the United States of America 102, (2005), pp. 755-760.

Zheng, J.H, "Two-step enhanced cancer immunotherapy with engineered *Salmonella typhimurium* secreting heterologous flagellin", Sci. Transl. Med. 9, (2017), p. 10.

"International Application Serial No. PCT/US2020/027302, International Search Report mailed Jul. 9, 2020", 3 pgs.

"International Application Serial No. PCT/US2020/027302, Written Opinion mailed Jul. 9, 2020", 7 pgs.

Wong, S, "Treating cancer with infection: a review on bacterial cancer therapy", Letters in Applied Microbiology, 61, (2015), 107-112.

"European Application Serial No. 20787821.6, Extended European Search Report mailed Jul. 26, 2023", 10 pgs.

"Canadian Application Serial No. TBD, Voluntary Amendment Filed Aug. 4, 2023", 6 pgs.

"International Application Serial No. PCT US2022 070578, International Preliminary Report on Patentability mailed Aug. 24, 2023", 8 pgs.

"International Application Serial No. PCT US2022 070582, International Preliminary Report on Patentability mailed Aug. 24, 2023", 9 pgs.

"International Application Serial No. PCT US2022 070583, International Preliminary Report on Patentability mailed Aug. 24, 2023", 11 pgs.

"Korean Application 10-2023-7030694, Voluntary Amendment Filed Sep. 8, 2023", W English Claims, 14 pgs.

Jung, Eun, "*Salmonella typhimurium* Suppresses Tumor Growth via the Pro-Inflammatory Cytokine Interleukin", Theranostics, vol. 5, No. 12, (Jan. 1, 2015), 1328-1342.

K, Brooks Low, "Lipid A mutant *Salmonella* with suppressed virulence and TNFa induction retain tumor-targeting in vivo", Nature Biotechnology, vol. 17, (Jan. 1, 1999), 5 pgs.

Lee, C-H, "Systemic administration of attenuated *Salmonella choleraesuis* in combination with cisplatin for cancer therapy", Molecular Therapy, Elsevier Inc, US, vol. 11, No. 5, (May 1, 2005), 10 pgs.

P, Gopinath, "Cancer Nanotheranostics", Springer, Singapore, (Mar. 11, 2015), 94 pgs.

(56) References Cited

OTHER PUBLICATIONS

Shi, Hui, "Protein analysis based on molecular beacon probes and biofunctionalized nanoparticles", Science China Chemistry; The Press, Sience China Press, vol. 53, No. 4, (Apr. 1, 2010), 16 pgs.
"Japanese Application Serial No. 2023-573019, Notification of Reasons for Refusal mailed Feb. 6, 2024", w machine English Translation, 5 pgs.
"European Application Serial No. 22753544.0, Response to Communication pursuant to Rules 161(1) and 162 EPC filed Feb. 21, 2024".
"European Application Serial No. 20787821.6, Response filed Feb. 26, 2024 to Extended European Search Report mailed Jul. 26, 2023", 5 pgs.
"Canadian Application Serial No. 3,210,760, Examiners Rule 86(2) Report mailed Aug. 14, 2024", 9 pgs.
"Japanese Application Serial No. 2023-573019, Notification of Reasons for Refusal mailed Jul. 24, 2024", w English translation, 8 pgs.
J., E. Karlinsey, "Completion of the hook-basal body complex of the *Salmonella typhimurium* flagellum is coupled to FlgM secretion and fliC transcription", Molecular Microbiology, 2000 vol. 37 (5), (2000), 1220-1231.
Smith, R. L., "Magnesium transport in Salmonella typhimurium. regulation of mgtA and mgtCB during invasion of epithelial and macrophage cells", Microbiology, vol. 144, (1998), 1835-1843.
Zhang, X., "An auto-inducible *Escherichia coli* lysis system controlled by magnesium", J. Microbiol. Meth., Vo. 79, (2009), 6 pgs.

\* cited by examiner

LOCALIZATION OF PAYLOAD DELIVERY SYSTEMS TO TUMOR SITES VIA BEACON CELL TARGETING

PRIORITY OF INVENTION

This application is a U.S. National Stage filing under 35 U.S.C. § 371 of PCT Patent Application No. PCT/2020/027302, filed on Apr. 8, 2020, which claims the benefit of priority under 35 U.S.C. § 119 (e) to U.S. Provisional Patent Application Ser. No. 62/831,122, filed Apr. 8, 2019, which are hereby incorporated by reference for all purposes.

BACKGROUND OF THE INVENTION

Cancer is generally characterized by an uncontrolled and invasive growth of cells. These cells may spread to other parts of the body (metastasis). Conventional anticancer therapies, consisting of surgical resection, radiotherapy and chemotherapy, can be effective for some cancers/patients; however, they are not effective for many cancer sufferers. Thus, further medical treatments are needed.

The role of bacteria as an anticancer agent has been recognized for over 100 years, and many genera of bacteria, including but not limited to *Clostridium, Bifidobacterium, E. coli, L. monocytogenes* and *Salmonella*, have been shown to preferentially accumulate in tumor tissue and cause regression.

The use of *Salmonella typhimurium* to treat solid tumors began with the development of a nonpathogenic strain, VNP20009. Well-tolerated in mice and humans, this strain has been shown to preferentially accumulate (>2000-fold) in tumors over the liver, spleen, lung, heart and skin, retarding tumor growth between 38-79%, and prolonging survival of tumor-bearing mice. In initial clinical trials, *S. typhimurium* was found to be tolerated at high dose and able to effectively colonize human tumors.

SUMMARY OF THE INVENTION

This invention pertains to the use of bacteria, in general, as a 'beacon cell' within cancerous tissues. In one embodiment, gram-negative bacteria are used. In another embodiment, facultative anaerobic bacteria are used. In another embodiment, *Salmonella, E. Coli*, and/or *L. monocytogenes* are used. In another embodiment, *Salmonella* is used, including strains of *Salmonella*. In one embodiment, attenuated strains of *Salmonella* are used. In one embodiment strains of *Salmonella typhimurium* are used. In another embodiment, attenuated strains of *Salmonella typhimurium* are used.

Provided herein is a cancer treatment that combines bacterial therapy with targeted delivery systems to deliver a payload (e.g. drug, prodrug, etc.) to cancerous tissue. Conventional medicines are limited by an inability to distinguish healthy cells from cancerous cells, which leads to nonspecific biodistribution of a given therapy and therefore debilitating side effects to patients. Additionally, modern cancer targeting treatments are designed to target chemicals (e.g. genes, proteins, peptides, etc.) that are not ubiquitously expressed by many cancer types and/or tumors found in patients. The present invention bypasses these limitations by presenting a bacteria-based chemistry, i.e. chemistries unique to bacteria and bacterial pathways and expressions, within tumor tissue that payload systems can be tailored to target. The cancer treatment accumulates only in bacteria-infected tumors and metastases while avoiding healthy tissue. The wide range of targetable tumors and metastases by the bacteria enables treatment again a multitude of cancer types and tumor sizes therefore improving the efficacy and safety of cancer treatment. Furthermore, the mechanical mobility of bacterial cells in tumors may cause faster and deeper transport of nanoparticles into tumor tissue.

Specifically, facultative anaerobic species of bacteria, including but not limited to *Salmonella, E. coli*, and/or *L. monocytogenes* can provide better transport than obligate anaerobes. Because facultative anaerobic species thrive in oxygen-rich conditions in the body, they can provide active transport of nanoparticles from the edges of the tumors to the inside. Obligate anaerobes, such as *C. difficile*, may not be able to provide this same active transport from the blood vessels since they only thrive in low oxygen environments, and therefore are unlikely to be found within close proximity to blood vessels.

One embodiment provides a nanoparticulate delivery systems targeting tumor-associated "beacon" cells in tumors.

One embodiment provides a nanoparticulate delivery system targeting tumor-associated bacteria in tumors.

Another embodiment provides a nanoparticulate delivery system with surface-bound antibodies or antibiotic moieties to target bacteria in tumors.

One embodiment provides an albumin based nanoparticulate delivery system with surface-bound antibodies or antibiotic moieties to target bacteria in tumors.

One embodiment provides an albumin based nanoparticulate delivery systems with surface-bound antibodies or antibiotic moieties to target the bacteria in tumors where the nanoparticle contains paclitaxel (as a payload).

Another embodiment provides a nanoparticulate delivery system with surface-bound antibodies or antibiotic moieties to target gram-negative bacteria in tumors where the nanoparticle contains a payload.

Another embodiment provides a nanoparticulate delivery system with surface-bound antibodies or antibiotic moieties to target facultative anaerobic bacteria in tumors where the nanoparticle contains a payload.

Another embodiment provides a nanoparticulate delivery system with surface-bound antibodies or antibiotic moieties to target *Salmonella* and/or *E. Coli* in tumors where the nanoparticle contains a payload.

Another embodiment provides an albumin based nanoparticulate delivery system with surface-bound *Salmonella*-specific antibodies or antibiotic moieties to target the *Salmonella* in tumors where the nanoparticle contains paclitaxel (as a payload).

BRIEF DESCRIPTION OF THE DRAWINGS

FIG. 7 is a representation of the overarching concept of this invention: targeting of tumors in vivo using *Salmonella*-specific antibodies to deliver a chemotherapy to bacteria-infected cancerous tissue. Objects depicted in the image are not to scale.

DETAILED DESCRIPTION OF THE INVENTION

Figure 1:
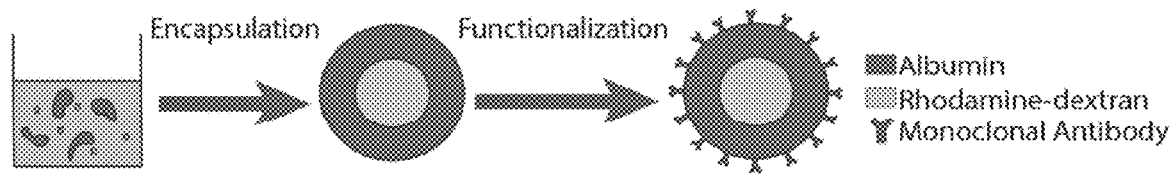
FIG. 1 illustrates the formation, encapsulation, and functionalization of nanoparticles. Albumin nanoparticles were used to encapsulate rhodamine-dextran. After encapsulation, nanoparticles were functionalized with *Salmonella*-specific antibody.

One major challenge in cancer treatment is developing a payload delivery system that specifically accumulates in tumors. Lack of tumor-specific targeting results in low therapeutic efficacy, high toxicity to off-target tissues, and reduction in the patient's quality of life. In response to this challenge, researchers have designed delivery systems to target chemicals (e.g. genes, proteins, peptides, etc.) specific to tumor tissue. However, chemicals expressed by cancer cells, such as folate receptors, are not ubiquitously expressed by many or all cancer types and are not necessarily specific to cancerous tissue. Moreover, the level of chemical expression from tumors is variable from patient to patient. Modern delivery systems face yet another challenge: transportation of payload into the tumor. Payload systems cannot easily penetrate deeply and/or quickly into tumors. Surprisingly, the instant invention overcomes these challenges by utilizing noncancerous cells in tumors as beacons for targeted delivery of therapeutic payloads. The result is a cancer treatment that significantly enhances accumulation, transport, and penetration of a given payload in tumor tissue, thereby diminishing side effects and improving efficacy and safety compared to conventional technology. Furthermore, the invention broadens the scope of targetable cancers, especially for cancers that are difficult or impossible to target with contemporary payload delivery systems.

Bacterial vectors can enable two therapeutic effects for the particles: 1) longer retention of the particles in tumors due to binding of nanoparticles to bacteria within the tumor, and 2) better transport into the tumor for bacteria that are mobile. The active transport effect is amplified with bacterial species that can occupy more oxygen rich tumor environments, such as facultative anaerobes. The outskirts of developed tumors receive more oxygen compared to a necrotic, poorly vascularized section of a tumor. Because these portions of the tumor are closer to available blood streams, bacteria that can live in more oxygen rich environments (e.g. facultative anaerobes) will be able to localize near blood vessels and therefore provide active transport of nanoparticles into the tumor once from the blood vessel either before or after crossing endothelial barriers. Facultative anaerobic bacteria, such as *Salmonella* and *E. Coli*, are examples of tumor targeting bacteria that proliferate in tumors and are capable of thriving in oxygen rich and deficient environments. Obligate anaerobic bacteria, such as *C. difficile* and *B. breve*, thrive in low oxygen environments. Tumor tissue capable of culturing obligate anaerobes is typically poorly vascularized. Therefore, it will be difficult and much less likely for a nanoparticle, either in the blood stream or in living, oxygen-rich tumor tissue to find obligate anaerobic bacteria to bind to compared to facultative anaerobic bacteria. The obligate anaerobic species may only provide retention effects of functional nanoparticles once particles passively diffuse into necrotic portions of the tumor, but are not likely to provide active transport from or near the blood vessel into the tumor tissue because they are unlikely to exist near the blood vessels where treatment is needed. Passive transport alone, is likely to result in lower accumulation values of nanoparticles, and therefore a less efficacious and safe treatment for patients when an obligate anaerobe is used compared to facultative anaerobes.

Provided herein, a payload is functionalized directly or encapsulated in a functionalized material to target noncancerous cells (e.g. bacterial cells which colonize tumor tissue) amongst cancer cells. The approach is general and is intended for use in any delivery system which targets "beacon" cells within cancerous tissue. A specific example of the technology, described later in this document, is the use of dextran-loaded albumin nanoparticles functionalized with antibody to target *Salmonella* beacons in tumor tissue.

The proposed functionalized delivery platforms can target various molecular sequences (e.g. peptide, protein, ligand, etc.) expressed by cells, including those found on bacteria. Some bacteria, such as *Salmonella typhimurium*, *E. coli*, and *L. monocytogenes*, are capable of specifically colonizing tumor sites in mammalian organisms in a ratio up to 10,000 to 1 compared to healthy tissue. Bacterial membranes are chemically dissimilar from mammalian membranes, and therefore can be targeted with functional groups (e.g. antibodies, aptamers, proteins, polymers, oligomers, monomers, surfactants, ligands, etc.) that will not target mammalian cells. By populating tumors with chemically distinct "beacon" cells, the previously non-targetable or difficult-to-target tumors will be targetable by the present invention. Payload delivery systems described herein may also achieve faster and deeper tumor penetration due to the mobility of "beacon" cells, especially bacterial cells with motility-enhancing organelles (i.e. flagella).

Aside from delivery of chemotherapy or cancer drugs to tumors populated with bacteria, the invention is applicable to any therapy platform that uses ligands to deliver a payload to tumors by targeting any "beacon" cell among tumor tissue, where the payload is any agent useful at directly or indirectly stopping, suppressing, detecting or killing cancer cells. Such a system can include use of not only therapies such as chemotherapy, but also systems which require an external stimulus once the nanoparticles have accumulated in tumors, including but not limited to systems that are activated photothermally, ultrasonically, or magnetically.

This invention can be extended to, but not limited to, the beacon-directed delivery of any payload (e.g. complex and simple molecules, proteins, etc.) to cancer cells that provide the following direct or indirect effects: Death of cancer cells, activation of or synergistic action with bacteria and/or human cells (e.g. cancer, immune, stromal, and/or any somatic cells) to provide anti-cancer effects, inhibition of cancer cell growth, proliferation, or metastasis, bacterial and/or human cell expression of any anti-cancer molecules or signals including but not limited to apoptosis signals or growth inhibitors, triggering of the immune system leading to direct or indirect anti-cancer effects, cell bursting of tumor or bacterial and/or human cells which leads to direct or indirect anti-cancer effects, promote bacterial proliferation within or among tumor tissue, provide payloads for external factors that trigger the payloads to induce an aforementioned effect, such as photodynamic therapy which uses a specific wavelength of light to activate oxygen which causes cell death, destabilization and/or release of a payload induced by the conjugation of delivery system to a beacon cell and/or signals, including but not limited to fluorescent signals, that enable detection of tumor tissue.

In embodiments where this invention is used for detection, some facultative anaerobes have been known to colonize tumor tissue as thin as five cell layers thick. Such as system is therefore capable of detecting and/or treating cancer at earlier stages and metastases. This is significant given that some bacteria, such as obligate anaerobes (*C. difficile, B. breve*) will not enable detection and/or treatment of these earlier stages of cancer given that these earlier cancer tissues do not provide the necrotic, low-oxygen environment that obligate anaerobes need in order to colonize and proliferate.

Further, it is noted that this invention does not only apply to nanoparticle delivery platforms, but any platform in which a ligand (e.g. small molecules, aptamers, proteins, antibodies, etc.) is attached to a payload and/or payload-encapsulating material and that ligand-payload system accumulates in tumor tissue via beacon-directed targeting. The invention is described herein in relation to bacterial beacons. However, the technology can be used to target any noncancerous cell that presents a unique chemistry within tumors.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, several embodiments with regards to methods and materials are described herein. As used herein, each of the following terms has the meaning associated with it in this section.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The articles "a" and "an" are used herein to refer to one or to more than one (i.e. to at least one) of the grammatical object of the article. By way of example, "an element" means one element or more than one element.

The phrase "and/or," as used herein, should be understood to mean "either or both" of the elements so conjoined, e.g., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, e.g., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

The terms "individual," "subject," and "patient," are used interchangeably herein and refer to any subject for whom diagnosis, treatment, or therapy is desired, including a mammal. Mammals include, but are not limited to, humans, farm animals, sport animals and pets. A "subject" is a vertebrate, such as a mammal, including a human. Mammals include, but are not limited to, humans, farm animals, sport animals and companion animals. Included in the term "animal" is dog, cat, fish, gerbil, guinea pig, hamster, horse, rabbit, swine, mouse, monkey (e.g., ape, gorilla, chimpanzee, orangutan) rat, sheep, goat, cow and bird.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease.

The terms "inhibit", "inhibiting", and "inhibition" refer to the slowing, halting, or reversing the growth or progression of a disease, infection, condition, group of cells, protein or its expression. The inhibition can be greater than about 20%, 40%, 60%, 80%, 90%, 95%, or 99%, for example, compared to the growth or progression that occurs in the absence of the treatment or contacting.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" is an amount sufficient to effect beneficial or desired result, such as preclinical or clinical results. An effective amount can be administered in one or more administrations.

The terms "cell," "cell line," and "cell culture" as used herein may be used interchangeably. All of these terms also include their progeny, which are any and all subsequent generations. It is understood that all progeny may not be identical due to deliberate or inadvertent mutations.

As used herein, an "instructional material" includes a publication, a recording, a diagram, or any other medium of expression which can be used to communicate the usefulness of the ligand of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

As used herein, the term "pharmaceutically-acceptable carrier" means a chemical composition with which an appropriate compound or derivative can be combined and which, following the combination, can be used to administer the appropriate compound to a subject. "Pharmaceutically acceptable" means physiologically tolerable, for either human or veterinary application. As used herein, "pharmaceutical compositions" include formulations for human and veterinary use.

By the term "specifically binds to", as used herein, is meant when a compound or ligand functions in a binding reaction or assay conditions which is determinative of the presence of the compound in a sample of heterogeneous compounds, or it means that one molecule, such as a binding moiety, e.g., an oligonucleotide or antibody, binds preferentially to another molecule, such as a target molecule, e.g., a nucleic acid or a protein, in the presence of other molecules in a sample.

The terms "specific binding" or "specifically binding" when used in reference to the interaction of a peptide (ligand) and a receptor (molecule) also refers to an interaction that is dependent upon the presence of a particular structure (i.e., an amino sequence of a ligand or a ligand binding domain within a protein); in other words the ligand comprises a structure allowing recognition and binding to a specific protein structure within a binding partner rather than to molecules in general. For example, if a ligand is specific for binding pocket "A," in a reaction containing labeled peptide ligand "A" (such as an isolated phage displayed peptide or isolated synthetic peptide) and unlabeled "A" in the presence of a protein comprising a binding pocket A the unlabeled peptide ligand will reduce the amount of labeled peptide ligand bound to the binding partner, in other words a competitive binding assay.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

Methods involving conventional molecular biology techniques are described herein. Such techniques are generally known in the art and are described in detail in methodology treatises, such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22: 1859-1862, 1981, and Matteucci et al., J. Am. Chem. Soc. 103:3185, 1981.

As used herein, the terms "including," "includes," "having," "has," "with," or variants thereof, are intended to be inclusive similar to the term "comprising."

The terms "comprises," "comprising," and the like can have the meaning ascribed to them in U.S. Patent Law and can mean "includes," "including" and the like. As used herein, "including" or "includes" or the like means including, without limitation.

Overview of Composition/Methods

The proposed invention is extended to any delivery system that targets tumor-associated "beacon" cells.

Current targeting methods, both passive and active, lack the ability to target a tumor with high specificity. While active targeting is possible, currently employed methods of cancer targeting rely on distinguishing cancer cells and/or environments from other mammalian cells and environments. This method has proven to be a difficult task in a biologically relevant environment and does not significantly improve effects compared to non-targeting methods. Furthermore, modern targeted therapies can only target specific types of cancers and only a fraction of patients are eligible for treatment based on the level of gene or chemical expression of cancer cells. Other methods, without active targeting abilities, rely on passive diffusion and the enhanced permeation and retention effect to deliver a payload to tumors.

Passive diffusion is generally less specific than active targeting mechanisms and therefore leads to accumulation of toxic drug in healthy tissues.

Surprisingly, bacteria can be used a target, or "beacon," to drastically increase accumulation of a payload in tumors and metastases while inhibiting delivery to noncancerous cells. Bacteria have already been shown to specifically colonize tumors. This invention exploits the chemically distinct surface of bacteria and uses them as targeting beacons in tumors and metastases. The invention provides improved targeting and tumor selectivity compared to modern therapies such as Doxil and Abraxane. Improved targeting will drastically improve localization of a payload to its respective target, and therefore increased efficacy. The increased specificity also diminishes damage to healthy tissues and organs, as the payload of interest will be entirely or primarily delivered to tumor tissue populated with bacterial cells. Beyond increasing localization of nanoparticles in tumor tissue, the mobility of bacteria, especially flagella-containing species, can also increase the transport of nanoparticles deeper and faster into tumors.

In one embodiment of the invention, the invention delivers a payload to tumors with bacterial beacons, such as *Salmonella*-infected tumors, therefore improving efficacy and decreasing dosage to healthy tissues. Additionally, some delivery systems, such as functionalized liposomes, may undergo accelerated destabilization and furthermore, release of encapsulated material facilitated by the motion of mobile bacteria such as *Salmonella typhimurium*. This may be particularly significant when the flagellin of *Salmonella typhimurium* is targeted where flagellin is a component of flagella, a moving bacterial organelle. Previous studies have shown that the strong stability of some nanoparticle delivery platforms, such as Doxil (i.e. liposomal doxorubicin), often do not release their payload and therefore diminish the therapeutic efficacy. Functionalized and loaded nanoparticles proposed herein will provide enhanced efficacy of cancer treatment by utilizing both active targeting of bacterial beacons and controlled release of the payload when the ligand-payload conjugate reaches its bacterial target in tumors. Furthermore, bacteria can be used to chemically trigger release of the nanoparticle payload. For example, bacteria can be used to produce express a chemical or enzyme that releases or activated a given payload.

The present invention improves therapeutic efficacy, tumor transport, and tolerability of cancer therapy by utilizing, in one embodiment, bacterial beacon-direct delivery to localize a payload specifically in tumor sites populated by bacteria. The present invention broadens the scope of targetable cancers and treatable patients. The invention also proposes a potential mechanism for accelerated and/or controlled release once the nanoparticle localizes into the tumor site.

The invention can also be used to deliver an inactive treatment that becomes activate in tumor tissue either from an external stimulus, where an external stimulus includes but is not limited to expression of a chemical or enzyme from bacteria, mechanical activation by bacteria, expression of chemicals from the tumor environment, release of chemicals from a synergistic nanoparticle system that contains a second payload, photothermal activation, ultrasonic activation, and/or magnetic activation.

I. Delivery System/Nanoparticles and Nanoparticle Materials

The delivery vehicle can be nanoparticles, microparticles, liquid crystals, liposomes, protein complexes, or molecules or the payload itself. The delivery vehicles may consist of any material or combination of materials such as proteins such as albumin and/or ferritin, phospholipids such as dioleylphosphateidylethanolamine and/or dioleylphosphatidylcholine, polymers such as poly(lactic-co-glycolic) acid, poly (lactic acid), polyethylene glycol, polyethylenimine, polymethylmethacrylate, polyhydroxyalkanoate, triblock copolymers of poly(ethylene oxide) and/or poly(propylene oxide), and/or inorganic materials such as gold, silver, titania, alumina, and/or silica. A variety of different nanoparticle materials can be used, some of which are listed in Table 1 below. Adding to this this list are proteins, such as, gelatin, elastin, gliadin, legumin, zein, whey proteins, milk proteins, and soy proteins. Note that any of these nanoparticles system can easily be functionalized with ligands of interest therefore enabling a wide array of delivery vehicles.

II. Bacteria

Tumor-targeting bacteria strains of interest include but are not limited to: *Salmonella, Mycobacterium, Streptococcus, Clostridium, Bifidobacterium, Listeria, Escherichia*, and, *Clostridia*. All listed bacteria can be targeted by a at least one or all of the below listed functional groups/ligand types.

This invention relates to the use of bacteria that can target, proliferate, and thrive in tumor tissue and tumor environments. One embodiment provides gram-negative bacteria. Another embodiment provides facultative anaerobic bacteria. Another embodiment provides *Salmonella* or *E. Coli*. One embodiment provides *Salmonella*. Another embodiment provides attenuated *Salmonella* strains, including VNP20009. In one embodiment the attenuated *Salmonella* strain is VNP20009.

III. Functional Groups/Ligands

Functional groups can include, but are not limited to, antibodies, aptamers, RNA, DNA, proteins, polymers, oligomers, monomers, and surfactants, that target, for example, bacteria (bacterial antigens) (note that ligand list is not all encompassing as myriad types of molecular sequences can be used to target "beacon" cells). Functional groups/ligands can be any particle, or simple or complex molecule, used to target any beacon cell, such as an antibody. In one embodiment, the functional groups are *Salmonella*-targeting polyclonal and/or monoclonal antibodies.

IV. Payload

The payload can be any agent that is useful in directly or indirectly stopping, suppressing, detecting, or killing the tumor with or without external stimulus. The payload may be a known agent that achieves any of the tasks mentioned above. One such payload/agent is paclitaxel.

Table 1 provides a list of marketed cancer therapies with active and/or passive targeting capabilities. Table 1 is not all encompassing, others may be included. A list of other types of cancer targeting medicines can be found at: cancer.gov/about-cancer/treatment/types/targeted-therapies/targeted-therapies-factsheet.

TABLE 1

List of marketed cancer technologies that utilize active and passive targeting of tumors.

| Drug/chemical technology | Description | Target |
|---|---|---|
| Abraxane | albumin-based nanoparticle (protein) chemotherapeutic: Paclitaxel | N/A (passive) |
| Doxil | liposomal nanoparticle (phospholipid) chemotherapeutic: Doxorubicin | N/A (passive |
| Tarceva | Epidermal growth factor receptor inhibitor | Epidermal growth factor receptor |
| Iressa | Epidermal growth factor receptor inhibitor | Epidermal growth factor receptor |
| Polymxin B | Antibacterial | Lipopolysaccharide |
| Polymxin E | Antibacterial | Lipopolysaccharide |
| Rituxan | Chimeric monoclonal antibody | CD20 (protein) |
| Velcade | Proteasome enzyme inhibitors | Proteasome enzyme complex |
| Rucaparib | Poly ADP-ribose polymerase enzyme inhibitor | Poly ADP-ribose polymerase enzyme inhibitor |
| Nexavar | Multi kinase inhibitor | Tyrosine protein kinases |
| Vyxeos | lipsomal nanoparticles (phospholipid) chemotherapeutic: Daunorubicin, Cytarabine | N/A (passive) |
| Daunoxome | lipsomal nanoparticles (phospholipid) chemotherapeutic: Doxorubicin | N/A (passive) |
| Myocet | lipsomal nanoparticles (phospholipid) chemotherapeutic: Doxorubicin | N/A (passive) |
| Caelyx | peglyated-liposimal nanoparticles (phospholipid) chemotherapeutic: Doxorubicin | N/A (passive) |
| Transdrug | poly(alkylcyanoacrylate) nanoparticles | N/A (passive) |
| Genxol-PM | methoy-PEG-polyactide nanoparticles (polymer) chemotherapeutic: Paclitaxel | N/A (passive) |
| Oncaspar | PEG-asparaginase nanoparticles (polymer-drug conjugate) modified enzyme: PEGylated L-asparagine amidohydrolase | N/A (passive) |

V. Cancer Treatment

Types of cancer that can be treated using the methods of the invention include, but are not limited to, solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

VI. Administration

The invention includes administration of bacteria as well as nanoparticles described herein and methods for preparing pharmaceutical compositions and administering such as well. Such methods comprise formulating a pharmaceutically acceptable carrier with one or more bacteria strains and/or nanoparticles described herein.

A pharmaceutical composition of the invention is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. Including agents, including bacteria, that have been frozen, cooled, or lyophilized.

For intravenous administration, suitable carriers include physiological saline, bacteriostatic water, Cremophor EL™ (BASF; Parsippany, N.J.) or phosphate buffered saline (PBS). It must be stable under the conditions of manufacture and storage and must be preserved against the contaminating action of other (undesired) microorganisms. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Injectable solutions can be prepared by incorporating the active compound in the required amount in an appropriate solvent with one or a combination of ingredients discussed above. Generally, dispersions are prepared by incorporating the active compound into a vehicle which contains a basic dispersion medium and various other ingredients discussed above. In the case of powders for the preparation of injectable solutions, the preferred methods of preparation are vacuum drying and freeze-drying which yields a powder of the active ingredient plus any additional desired ingredient from a previously.

Oral compositions generally include an inert diluent or an edible carrier. For example, they can be enclosed in gelatin capsules. For the purpose of oral therapeutic administration, the active compound can be incorporated with excipients and used in the form of tablets, troches, or capsules.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the bacteria and/or nanoparticles are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the bacteria are formulated into ointments, salves, gels, or creams as generally known in the art.

It can be advantageous to formulate compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

When administered to a patient bacterium, such as attenuated Salmonella, can be used alone or may be combined with any physiological carrier. In general, the dosage ranges from about 1.0 c.f.u./kg to about $1\times10^{12}$ c.f.u./kg; optionally from about 1.0 c.f.u./kg to about $1\times10^{10}$ c.f.u./kg; optionally from about 1.0 c.f.u./kg to about $1\times10^{8}$ c.f.u./kg; optionally from about $1\times10^{2}$ c.f.u./kg to about $1\times10^{8}$ c.f.u./kg; optionally from about $1\times10^{4}$ c.f.u./kg to about $1\times10^{8}$ c.f.u./kg; optionally from about $1\times10^{5}$ c.f.u./kg to about $1\times10^{12}$ c.f.u./kg; optionally from about $1\times10^{5}$ c.f.u./kg to about $1\times10^{10}$ c.f.u./kg; optionally from about $1\times10^{5}$ c.f.u./kg to about $1\times10^{8}$ c.f.u./kg.

EXAMPLE

The following example is provided in order to demonstrate and further illustrate certain embodiments and aspects of the present invention and are not to be construed as limiting the scope thereof.

Introduction

One major challenge in cancer treatment is developing a highly efficacious and safe cancer therapy that delivers a payload only to tumors and does not impart systemic toxicity to patients. Nanoparticle therapies have been developed and FDA approved, such as Abraxane, that encapsulate toxic payloads to prevent exposure of toxic drug to healthy tissue. Unfortunately, these therapies do not actively target cancer, and therefore chemotherapy-specific side effects remain. The FDA has approved various targeted cancer therapies including drugs such as trastuzumab. However, these therapies are limited to specific cancer types and not all tumor types can be treated. Modern targeted therapies must therefore be designed to be specific to cancer cells while avoiding targeting of healthy mammalian cells which can exhibit a similar surface chemistry.

Provided herein is a novel method for facile targeting of a broad range of cancers by utilizing chemically distinct bacteria as a targeting beacon. It has been shown that bacteria have a high propensity to colonize specifically in tumor tissue while largely avoiding healthy tissue. For example, Salmonella typhimurium inherently accumulate in neoplasms and can colonize tumors at ratios of 10,000:1 compared to healthy organs. Remarkably, Salmonella can target metastases as thin as five cell layers thick. Bacterial membranes exhibit a distinct surface composition and chemistry compared to mammalian cells, such as lipopolysaccharides and flagellin. Therefore, bacteria can serve as beacons in both tumors and small metastases present throughout the body. The localization of bacteria in cancerous tissue enables the efficacious and rapid delivery of functionalized payloads to cancerous tissue while preventing delivery and potentially damage to healthy cells.

Described herein is a payload that has been encapsulated in a functionalized nanoparticle and delivered to Salmonella-infected tumors in vitro and in vivo. Albumin was selected as a model nanoparticle material, Salmonella as a model bacterial cell, Salmonella-specific antibodies as a model functional group, and rhodamine-dextran, a fluorescent molecule, as a model payload. It demonstrated herein that 1) albumin nanoparticles can be controllably and reproducibly fabricated, 2) functional groups (i.e. antibodies) of interest bind to the intended target (i.e. Salmonella), 3) albumin nanoparticles can encapsulate a payload and nanoparticles can be functionalized with antibodies of interest, 4) functionalized nanoparticles specifically bind to the intended target (i.e. Salmonella), 5) functionalized nanoparticles target and localize in in vitro tumors leading to increased accumulation and transport of a payload into cancerous tissue, and 6) functionalized nanoparticles target and localize in in vivo tumors leading to increased accumulation into cancerous tissue. The approach is general and is intended for use with a multitude of bacteria, functional groups, and payloads for a wide array of applications in many different types of cancer.

Example 1

Production of Nanoparticles

Albumin nanoparticles were designed to match the particle size of 140 nm, similar to that of the FDA approved albumin nanoparticle delivery system, Abraxane. Controllable fabrication of albumin nanoparticles provides the platform for proving the concept of targeted delivery to tumors using bacterial beacons. Dynamic light scattering (DLS) was used to measure particle diameter.

Albumin nanoparticles have been synthesized via a desolvation technique, using ethanol as an antisolvent. Albumin is first dissolved in water followed by ethanol at a controlled rate. The ethanol causes precipitation of albumin in the form of nanoparticles. Nanoparticles are then crosslinked with glutaraldehyde to impart stability. The resulting nanoparticles were analyzed using DLS. Particles made in NaOH (aq, pH 10) have a diameter of 134.5±7.5 nm. This size is consistent with the FDA approved nab-paclitaxel formulation which has an average particle size of 140 nm.

Example 2

Antibody Binding to *Salmonella*

Before functionalizing the nanoparticles, the antibodies of interested were first tested for their ability to bind to *Salmonella* in solution. Specifically, fluorescent-antibodies are used for detection during the in vitro and in vivo experiments discussed below. The study proved that the antibodies successfully and specifically bind to *Salmonella* in solution which will allow nanoparticles to bind to the intended target, *Salmonella*.

The selected antibodies for this study were shown to bind to *Salmonella* suspended in phosphate buffer solution (PBS). This result demonstrates the ability for the functional antibodies to bind free swimming *Salmonella* and will enable nanoparticle targeting to bacteria.

Figure 2:
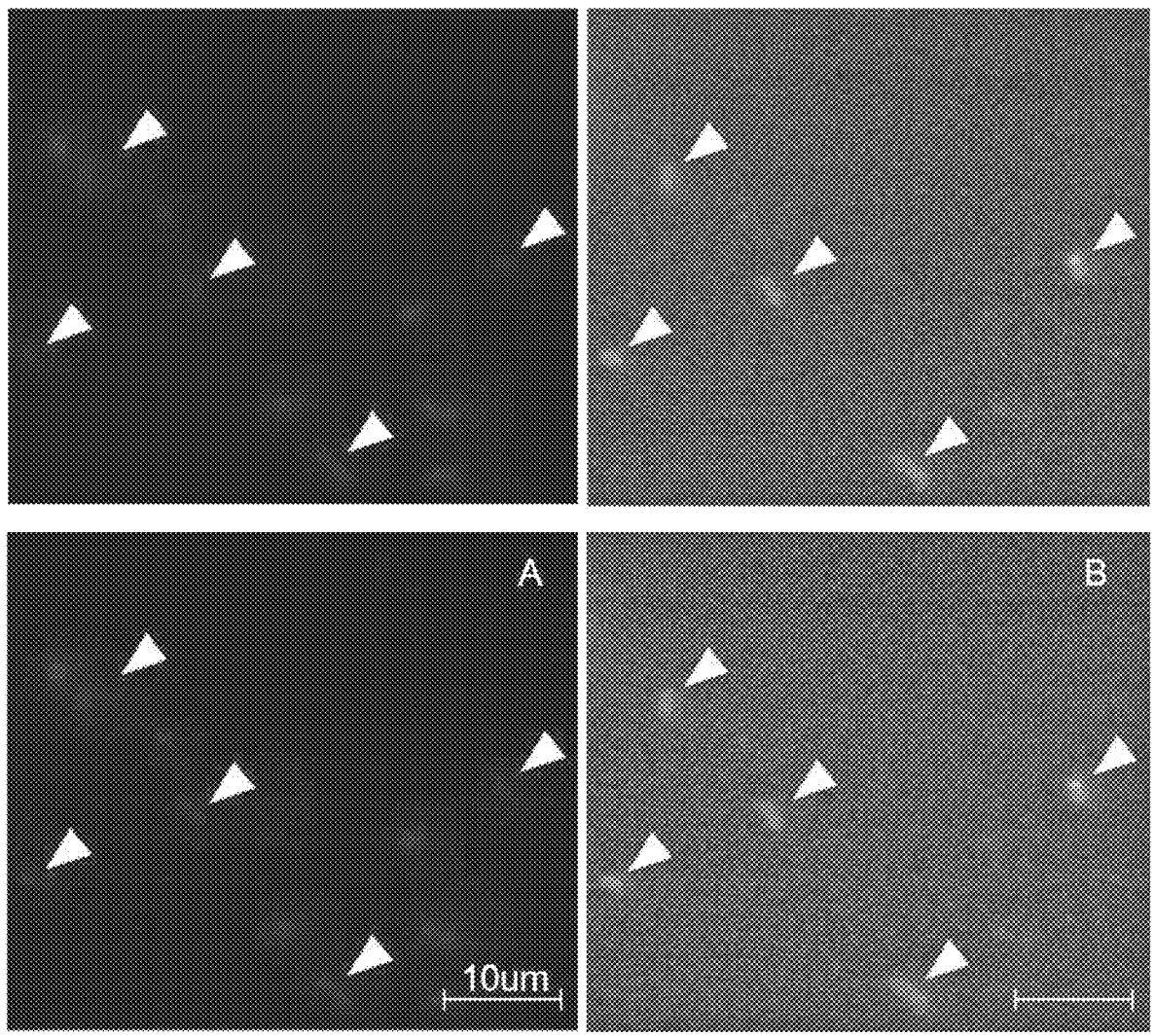
FIG. 2 depicts binding of FITC-labeled Antibody to DAPI-Stained *Salmonella* in suspension. A) Fluorescent microscope image of DAPI (blue) stained *Salmonella* in suspension. B) Fluorescent microscope image of FITC (green)-labeled antibodies attached to *Salmonella*. White arrows depict *Salmonella* cells which exhibit fluorescence from both DAPI and FITC, therefore showing that the FITC-labeled Antibody has bound to these cells.

Mounting media with DAPI, a blue fluorescent dye, was used to stain *Salmonella*. FITC-labeled antibody, specifically Ab69253 (a green fluorescent antibody) was pipetted into a suspension of stained *Salmonella* in PBS. The non-binding antibodies were removed via centrifugation and the *Salmonella* were resuspended in PBS. The suspension was then viewed using fluorescent microscopy. Fluorescent images reveal green fluorescence in proximity to blue-stained *Salmonella* (FIG. 2). Approximately 60% of the bacterial cells showed significant fluorescence from FITC and DAPI, indicating that 60% of the *Salmonella* was successfully targeted and bound by the antibody. This co-localization study demonstrates that the antibody binds to suspended *Salmonella*. Therefore, functionalized nanoparticles will bind to *Salmonella* in a fluid environment such as the extracellular space in tumor tissue. Typically, *Salmonella* populate tumors at a density of $10^8$-$10^9$ bacteria/g tumor which would give $0.60*10^7$-$0.60*10^8$ bacteria/g tumor that could be targeted in a given tumor.

Example 3

Encapsulate Model Payload and Functionalize Albumin Nanoparticles with Antibody

Rhodamine-dextran was encapsulated in albumin nanoparticles to serve as a model payload. The nanoparticles were functionalized with antibodies to provide targeting of bacterial beacons. Both rhodamine-dextran and the antibody were fluorescent, and therefore enabled the detection of nanoparticle accumulation in in vitro and in vivo studies discussed later. FIG. 1 illustrates the general concept of encapsulation and functionalization as pertains to this example.

Rhodamine-dextran (10,000 g/mol), a model payload, was successfully encapsulated in albumin nanoparticles. Following encapsulation, nanoparticles were functionalized with fluorescent *Salmonella*-specific antibody. Encapsulation and functionalization were verified via fluorescent microscopy. Stochastic Optical Reconstruction Microscopy (STORM) was used to verify the encapsulation of rhodamine (red fluorescent dye) in albumin nanoparticles and conjugation of fluorescent-labeled antibodies (Alexa 488 (green fluorophore) and Alexa 647 (blue fluorophore)) to the particle surface. Encapsulation of rhodamine-dextran and functionalization of nanoparticles enables the development of a payload delivery system that can target bacteria.

Rhodamine-dextran was encapsulated by adding it to the albumin nanoparticle synthesis procedure listed above. Note that rhodamine-dextran was added before ethanol to enable encapsulation during particle formation. Once rhodamine-dextran-encapsulated albumin nanoparticles (RNPs) were formed and crosslinked, Alexa 488 and 647 antibodies were incubated with 1-ethyl-3-(3-dimethylaminopropyl) carbodiimide (EDC) and n-hydroxysulfosuccinate (Sulfo-NHS) to activate the antibody for functionalization. Antibody was reacted for 5 minutes at room temperature on an orbital shaker. After 5 minutes, RNPs were added. The mixture reacted for 90 minutes on an orbital shaker at room temperature. The reaction mixture was then centrifuged at 20,000 g for 20 mins. The supernatant was removed and replaced with an equal volume of DI water. The centrifuged pellet, containing the functionalized nanoparticles, was ultrasonicated three times in 5 minutes intervals to resuspend the particles.

Figure 3:
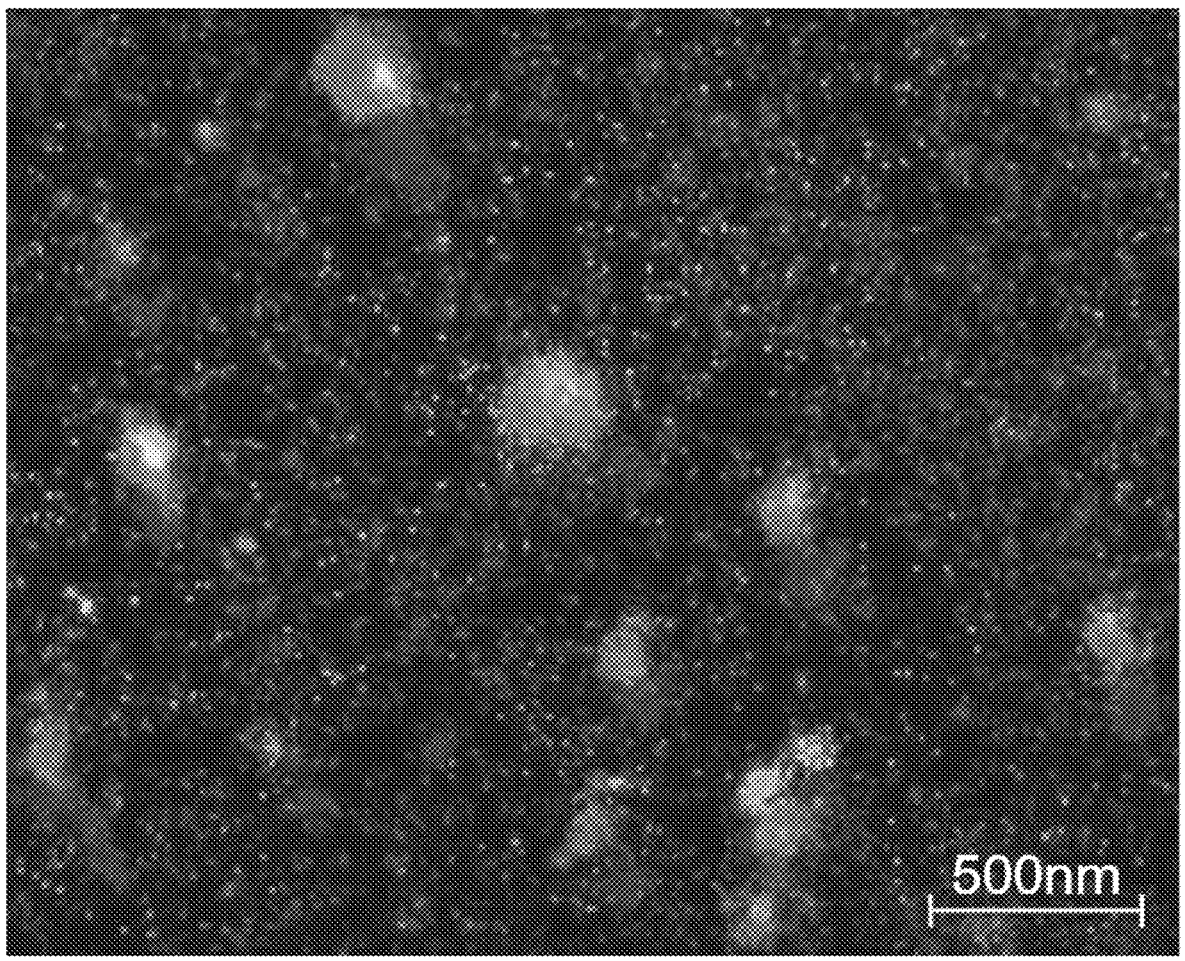
FIG. 3 depicts encapsulation of rhodamine-dextran dye and binding of Alexa 488 and 647 antibodies. Circular clusters of rhodamine-dextran (red) can be seen near clusters of Alexa 488-labeled antibody (green) and Alexa 647-labeled antibody (blue) thus showing that antibody is covalently bound to the nanoparticle surface.

Glass Bottom Culture Dishes (GBCD) were prepared for binding the functionalized nanoparticles to a surface for STORM imaging. Briefly, poly-L-lysine solution was dispensed onto the GBCD and reacted for 10 minutes. The liquid was removed, and suspended functionalized nanoparticles were dispensed onto the lysine-treated GBCD. The functionalized nanoparticles were incubated with a phosphate buffer solution (PBS) and formaldehyde for 45 minutes. The liquid was then removed and washed with PBS five times. STORM imaging was conducted by taking 20,000 fluorescent images for each fluorophore/dye: rhodamine-dextran (red), Alexa 488 (green), Alexa 647 (blue). The resulting images were compiled and reconstructed into a single image. As seen in FIG. 3, the red nanoparticles are found adjacent to green and blue clusters indicating that nanoparticles (red) are functionalized with antibody (green and blue). FIG. 3 shows the encapsulation of rhodamine-dextran and the covalent attachment of antibodies to the nanoparticle surface.

Example 4

Demonstration of Specificity of Functionalized Nanoparticles for Bacteria

The ability for functionalized nanoparticles to bind specifically to a desired *Salmonella* target was validated using fluorescent microscopy. Two groups of nanoparticles were designed for this experiment; one group was functionalized to target the *Salmonella* while the other group (control group) was designed to have nonspecific binding to *Salmo-* nella. The control group did not exhibit any noticeable binding while the Salmonella-specific nanoparticles showed significant binding. This demonstrates the ability for the invented payload system to target bacteria.

Functionalized nanoparticles were used to target Salmonella bound to a glass slide. Significant binding occurred for nanoparticles functionalized to target treated Salmonella. Fluorescent microscopy confirmed that significant binding occurred for nanoparticles functionalized to specifically target Salmonella in this study. The results demonstrate that the present invention can be designed for specific targeting of bacteria.

Figure 4:
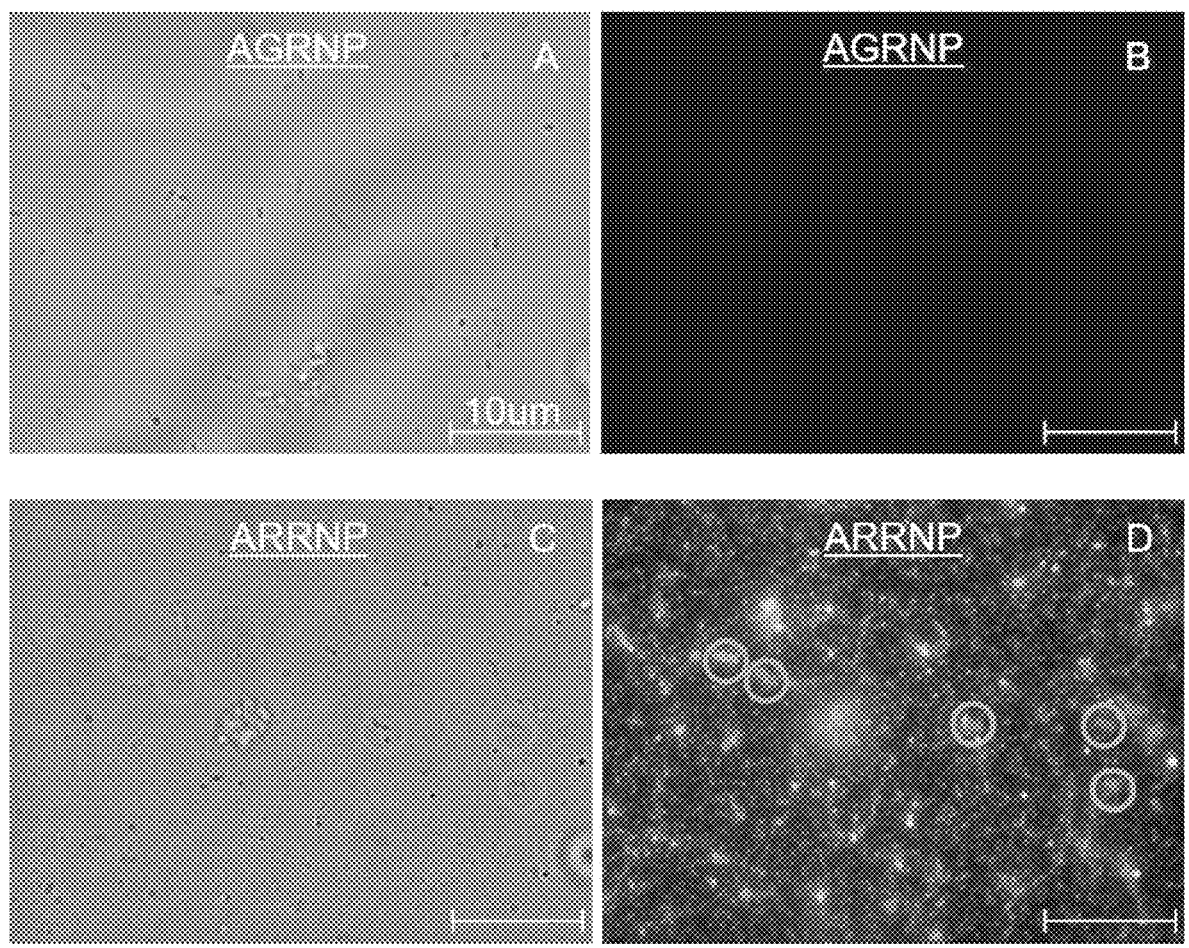
FIG. 4 depicts specific targeting of functionalized nanoparticles to *Salmonella*. A) Bright-field image of *Salmonella* bound to GBCD incubated with rabbit antibody and then AGRNPs. B) Red and green fluorescent image of picture 'A'. No binding of nanoparticles occurred, therefore there is no recognizable fluorescence. C) Bright-field image of *Salmonella* incubated with rabbit antibody and then ARRNPs. D) Red and green fluorescent image of picture 'C'. Significant binding to rabbit antibody-decorated *Salmonella* was accomplished using ARRNPs while AGRNPs did not bind to the *Salmonella*. Blue circles denote individual *Salmonella*.

Salmonella were bound to GBCDs with poly-L-lysine similar to the procedure performed for the STORM imaging procedure (see above). The bound Salmonella were then exposed to a solution containing non-fluorescent, Salmonella-specific rabbit antibody. After 1 hour, the antibody solution was removed and the GBCDs were washed 5 times with PBS multiple times to remove unbound antibody. RNPs were prepared as before. For this study, two groups of functionalized nanoparticles were synthesized. One group, serving as the control, was RNPs functionalized with Alexa 488 anti-goat antibody (AGRNPs), and another group was functionalized with Alexa 488 anti-rabbit antibody (ARRNPs). The ARRNPs were designed to provide specific binding to the Salmonella coated in rabbit antibody and the AGRNPs should not experience specific binding. The AGRNPs and ARRNPs were independently incubated in separate GBCD's with the rabbit-antibody treated Salmonella for 1 hour. Unbound nanoparticles were removed by washing the GBCD 5 times with PBS. The GBCD's were then imaged using brightfield and fluorescence imaging (red for rhodamine and green for Alexa 488). Images are displayed in FIG. 4.

When AGRNPs were used (FIGS. 4A and 4B), no nanoparticles can be seen bound to Salmonella when comparing the brightfield to the fluorescent images. However, the ARRNPs (FIGS. 4C and 4D) show significant binding to the Salmonella. Significantly, the red fluorescent signals are colocalized with green fluorescent signals, therefore showing that the nanoparticles can remain intact while also targeting bacteria specifically.

Example 5

Improved Localization, Penetration, and Accumulation of Functionalized Nanoparticles in In Vitro 3D Microfluidic Tumor Models 3D tumor models were prepared in a microfluidic device to simulate the intravenous environment near tumor masses in vivo. Functionalized nanoparticles were administered to bacteria-infected tumors in the microfluidic device for 24 hrs. Fluorescent microscopy was used to monitor accumulation and infiltration of nanoparticles into tumor tissue. The fluorescent antibody and model payload enabled detection of nanoparticles in tumors. Fluorescent images showed higher localization, and therefore accumulation, of nanoparticles in tumors infected with bacteria compared to control tumors which were not infected. The fluorescent images also suggest that rapid penetration, or transport, into the tumor may be mediated by the mobility of bacteria lending to a novel method of nanoparticle transport in tumors.

Nanoparticles were functionalized and delivered to 3D tumor models. Tumors containing Salmonella showed drastically increased accumulation of nanoparticles as depicted by the fluorescent images discussed below and shown in FIG. 6. The results from this study demonstrate the invention's propensity to deliver a payload specifically to tumor tissue by targeting bacterial beacons. Moreover, the movement of bacteria throughout the tumor can enhance the transport properties of the nanoparticles.

Figure 5:
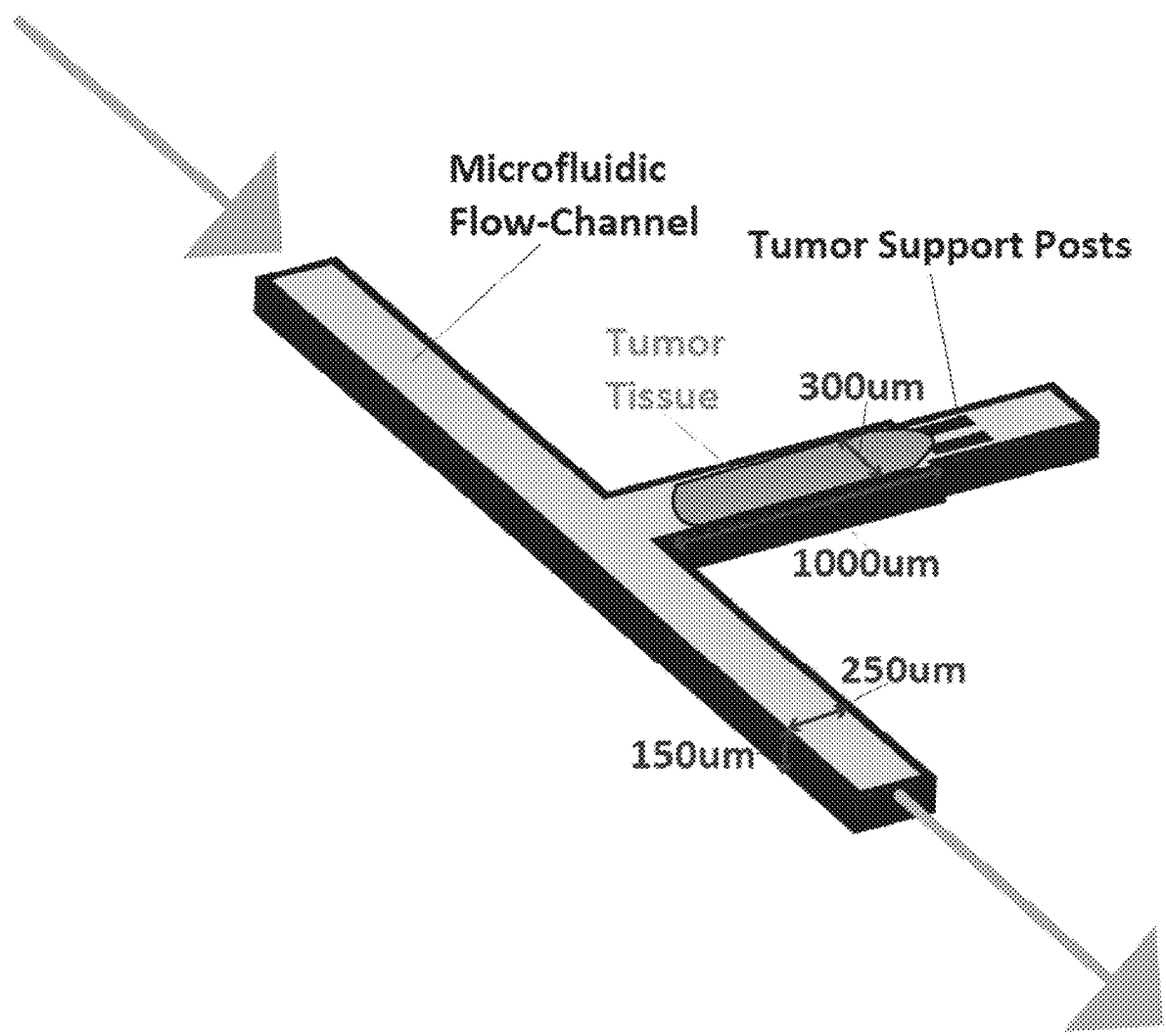
FIG. 5 provides a diagram of Microfluidic Device. The microfluidic device allows for packing of a 3D tumor model with a channel that mimics intravenous flow.

Microfluidic devices were used to demonstrate that functionalized nanoparticles can target bacteria in 3D tumor models, therefore providing specific accumulation in tumors. The device is composed of polydimethylsiloxane (PDMS) with four channels, each containing six positions for 3D tumor models (FIG. 5). The device was sanitized by flowing 30 minutes of 10% bleach solution and 70% ethanol solution, independently, through the device. Later HEPES media containing amphotericin B (anti-fungal) and carbenicillin (anti-bacterial) was flowed through the device for 30 minutes to remove trace bleach and ethanol. After 30 minutes, tumors were packed into the device and media was flowed through the device for one hour.

The tumors were divided into two groups; one group of tumors were infected with Salmonella, and the other group was Salmonella-free. Note that Salmonella used in this study are carbenicillin-resistant and ampicillin-resistant and therefore avoid being killed by carbenicillin and ampicillin, respectively. After administering Salmonella to the first group of tumors, all tumors had media flowed through for 12 hours. Separately, RNPs were functionalized with FITC-labeled Salmonella-specific antibody (FITC-RNPs). At 12 hours, the FITC-RNPs were administered to the microfluidic device for 24 hours. Brightfield and fluorescent images of the tumors were taken every 30 minutes to monitor the infiltration of nanoparticles into the cancerous tissue. Images from an experimental tumor and a control tumor are displayed in FIG. 6.

Figure 6:
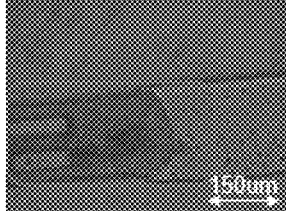
FIG. 6 provides time lapse images of FITC-RNP Administration to Tumor Models. The following images display a 24-hour time lapse of infiltration of FITC-RNPs into tumor models. Image groups are labeled with, 'A' or 'B', and a number, '1', '2', or '3'. The labels correspond to the following codes: 'A'—control tumors not infected with *Salmonella*, 'B'—tumors infected with *Salmonella*, '1'—brightfield images, '2'—Green Fluorescent images, and '3'—Red fluorescent images. Red boxes denote the 3D tumor masses.
Figure 7:
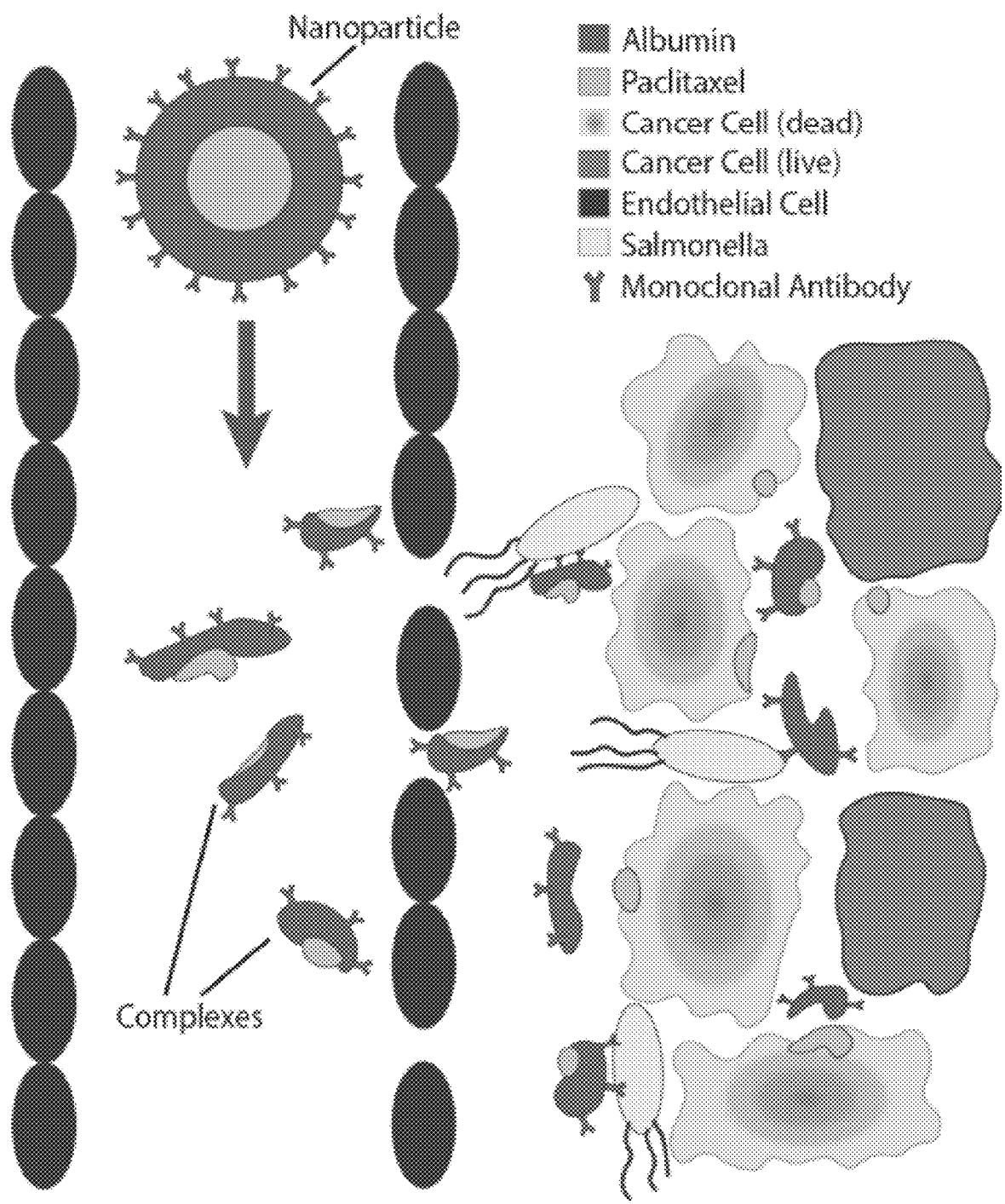
FIG. 7 provides a schematic of targeting of functionalized drug delivery platforms to bacteria localized in tumor tissue. In one delivery system, *Salmonella typhimurium* is used to invade tumor tissue to serve as beacon cells. Protein nanoparticles, specifically albumin nanoparticles, were functionalized with *Salmonella*-targeting monoclonal antibodies. The functionalized nanoparticles encapsulate a model payload, specifically rhodamine-dextran, and were delivered to the tumor tissue by targeting the *Salmonella*.

The images in FIG. 6 reveal that nanoparticles penetrate more deeply into tumors infected with nanoparticles. Significantly, the green and red fluorescent images corresponding to the Salmonella-infected tumors show the appearance of co-localized fluorescent marks as time moves forward. Interestingly, the colocalized marks show a sort of 'nanoparticle penetration front' moving deeper into the tumor from the 6 hr to 24 hr time points. This may be indicative of bacteria-mediated transport.

The results demonstrate that FITC-RNPs accumulate and penetrate deep into the tumor and may present a mechanism of enhanced transport properties mediated by the movement of bacteria throughout the tumor. The ability for nanoparticles to target and accumulate in tumors is vital for nanoparticle systems to deliver a payload to the tumors while avoiding healthy tissue.

Example 6

Salmonella Improve Intracellular Invasion of Functional Nanoparticles

A 2D cell invasion with a 4T1 tumor model was used to investigate the increase in intracellular invasion of nanoparticles into cancer cells. Briefly, 2D cultures were formed by incubating 100,000 4T1 cells in 24-well plates for 48 hrs in DMEM bicarbonate under 5% $CO_2$. Next, $3\times10^6$ cfu of GFP-expressing Salmonella (see Example 8) was added to each culture. Cultures were divided into two groups to receive two different types of particles: 1) control RNPs conjugated with an Isotype Antibody control (BioLegend Inc., Item no. 910801), and 2) RNPs functionalized with nonfluorescent, Salmonella-specific antibody. Both antibodies were bound to particles similar to the conjugation procedure described in Example 3. 50 uL of nanoparticles at 2.5 mg/mL in PBS were administered to each culture. After administration, the system was incubated for 2 hrs. The systems were then washed 5 times to remove any extracellular particles and bacteria. The systems were imaged using fluorescence microscopy. A 6.1-magnitude increase in particle accumulation was experienced for functional particles compared to the Isotype Control. This demonstrates that functional particles can bind to the bacteria and enter into cancer cells when bound to bacteria.

Example 7

Formation of Tumor Spheroids

Tumor spheroids were produced in order to study accumulation and retention of nanoparticles in tumors under stagnant, non-flowing conditions. Spheroids were generated using 15,000 MC38 cells in 200 uL of DMEM bicarbonate aliquoted into a tissue culture treated round bottom 96-well plate. The well plate was centrifuged at 1000 g for 10 minutes. Spheroids were incubated for 24 hrs in DMEM bicarbonate and then transferred to a tissue culture treated 24 well plate in 500 uL of DMEM bicarbonate. Spheroids were incubated for an additional 24 hours before being used in the in the Example 9.

Example 8

*Salmonella* Culture

Kanamycin-resistant, carbenicillin-resistant VNP20009 (*Salmonella*) were incubated in LB culture media with kanamycin and carbenicillin at 37° C. For some of the provided Examples, *Salmonella* were further engineered to express flagellin in presence of arabinose and are therefore more motile than their less-flagellated derivatives. For such Examples, the LB media also included addition of 10 uL/mL of 1M arabinose in PBS. Similarly, some examples include bacteria that have been engineered to express green fluorescent protein (GFP) independent of environmental conditions. Details of *Salmonella* used in each study are described in individual Examples. The biological modifications to the bacteria are expected to be easily replicated by one skilled in the art.

Example 9

Figure 8:
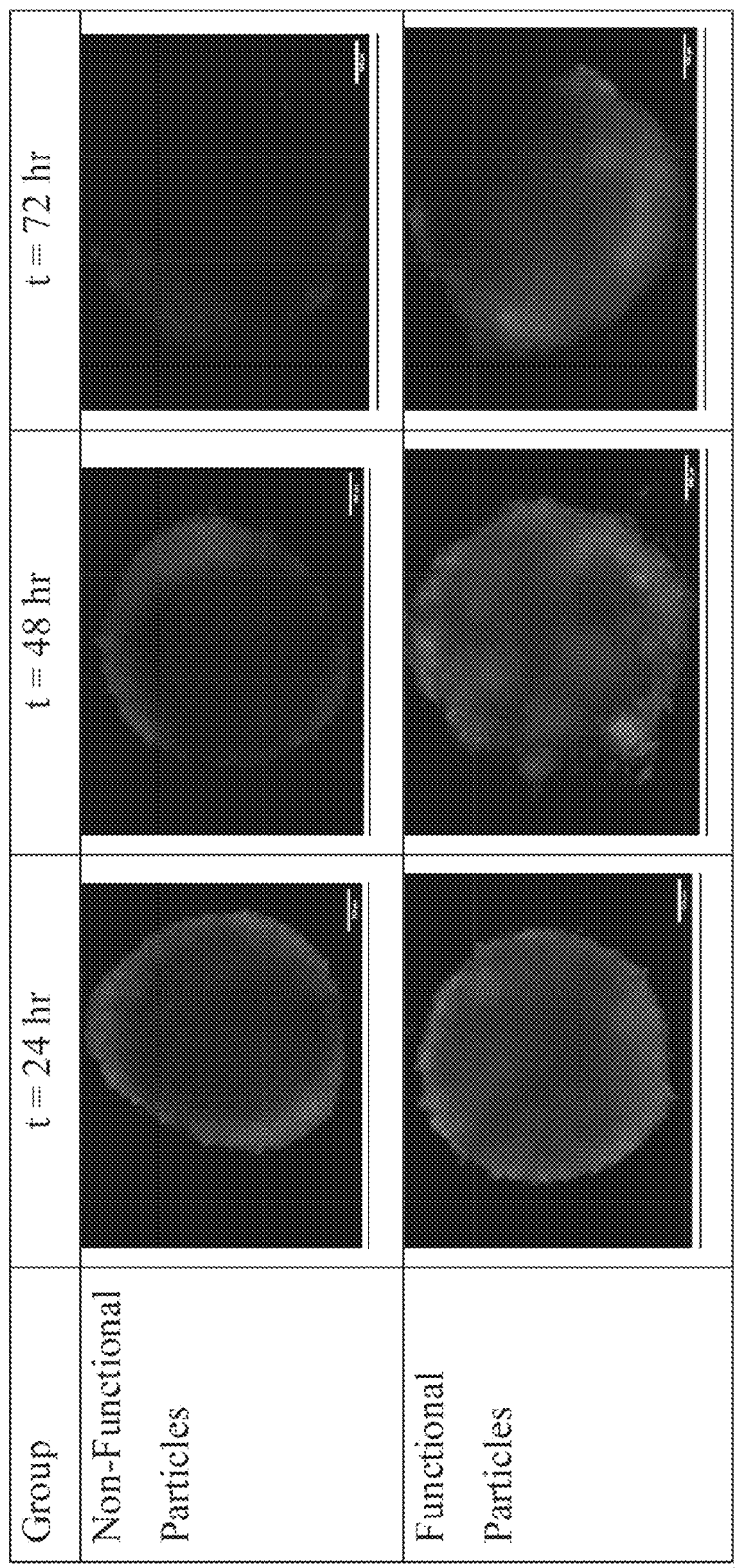
FIG. 8 demonstrates a visual difference between nanoparticle concentrations from both groups for the first 72 hours of the study.
Figure 9:
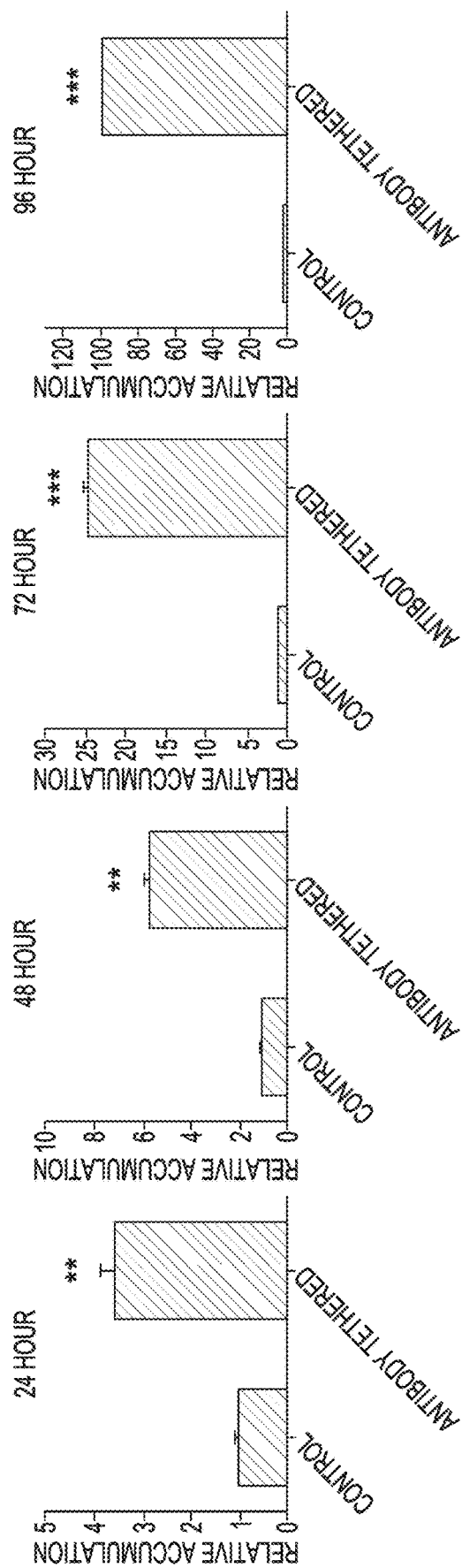
FIG. 9 displays plots showing the magnitude increase in fluorescence for functional nanoparticles compared to control particles at each timepoint from 24-96 hrs.

Improved Accumulation and Retention of Functionalized Nanoparticles in In Vitro 3D Tumor Models A 3D tumor model in well plates was used to demonstrate the improved nanoparticle accumulation and retention in cancerous tissue infected with bacteria. MC38 tumor spheroids were incubated with *Salmonella* for 4 hrs at 37° C. at 5% $CO_2$ in DMEM bicarbonate media. Following incubation, 100 uL of 2.5 mg/mL of nanoparticles in PBS were administered in two separate groups: 1) control group consisting of RNPs, and 2) functional nanoparticles with encapsulated rhodamine. Note functional particles in this Example refers to RNPs functionalized with nonfluorescent *Salmonella*-specific antibody (Abcam, ab35156) by methods previously described. Nanoparticles were incubated with tumors for 24 hrs in DMEM bicarbonate with 5 ug/mL of gentamicin to kill any bacteria outside the tumor spheroid. After the 24 hr incubation, three washes were performed where each wash contained a 1 hr incubation between each wash. Following the multi-hour washing procedure, the well plates containing tumor spheroids were quickly washed three more times and then imaged using fluorescence microscopy. The procedure was repeated for an additional 72 hours to demonstrate the increased retention of functional nanoparticles compared to the nonfunctional controls. Tumors were observed every 24 hrs. Images were analyzed using ImageJ and Matlab to quantify the differences in fluorescence intensity at various time points. Surprisingly, nanoparticle accumulation was 3.6-fold higher for the functional particles compared to the non-functional particles for the initial 24 hr nanoparticle incubation period. At the 48 hr time point, the fluorescence intensity was ~5.5-fold higher for functional particles compared to the control. For 72 hour timepoint the fluorescence intensity was about ~25-fold higher for functional particles compared to the control. Finally, at 96 hrs the nanoparticle accumulation for functional nanoparticles was ~100 times greater than the control group. Surprisingly, the results demonstrate that functionalized particles target bacteria in tumors causing higher initial nanoparticle accumulation as well as longer retention of the particles. A visual difference between nanoparticle concentrations from both groups can be seen in FIG. 8 for the first 72 hours of the study. FIG. 9 displays plots showing the magnitude increase in fluorescence for functional nanoparticles compared to control particles at each timepoint from 24-96 hrs. Note that in FIG. 9, 'antibody tethered' refers to the functional nanoparticles and 'control' refers to nonfunctional nanoparticles.

Example 10

Production of Fluorescent Particles for In Vivo Application

Albumin nanoparticles were synthesized with fluorescent-tagged albumin using thiol click-chemistry for in vivo application. Cy 5.5 dye was chosen as the fluorophore to minimize autofluorescence from biological tissue. Briefly, Cy 5.5 maleimide (purchased from ApexBio, Cat. No.: A8140-25) is reacted with 90 mg free albumin at pH 7.0 for 3-4 hrs in 1 mL of 0.01M solution of PBS at room temperature in a small glass vial under mild mixing conditions. A molar ratio of 1.33:1 of dye to protein was used. Following the reaction, the reaction contents were added to a solution of 90 mg albumin in NaOH (aq., pH 10). The protein cocktail is then subject to a desolvation procedure as specified in the Example 1 to form Cy 5.5 Fluorescent-Labeled Albumin Nanoparticles (CFANs). The resulting CFANs are centrifuged at 10,000 g for 10 mins. The supernatant is discarded to remove fluorescent molecules that did not condense into the nanoparticle phase. The resulting pellet is then resuspended using three 5-minute sonication baths. This washing procedure is repeated a total of 4 times. After the final wash, CFANs were dispersed in PBS. The particles were then functionalized with antibody as in Example 9 with non-fluorescent *Salmonella*-specific antibody and then used for in vivo studies described in Example 11. Control fluorescent nanoparticles were not functionalized with antibody and are herein referred to as Nonfunctional Fluorescent Nanoparticles (NFNs).

Example 11

Figure 10:
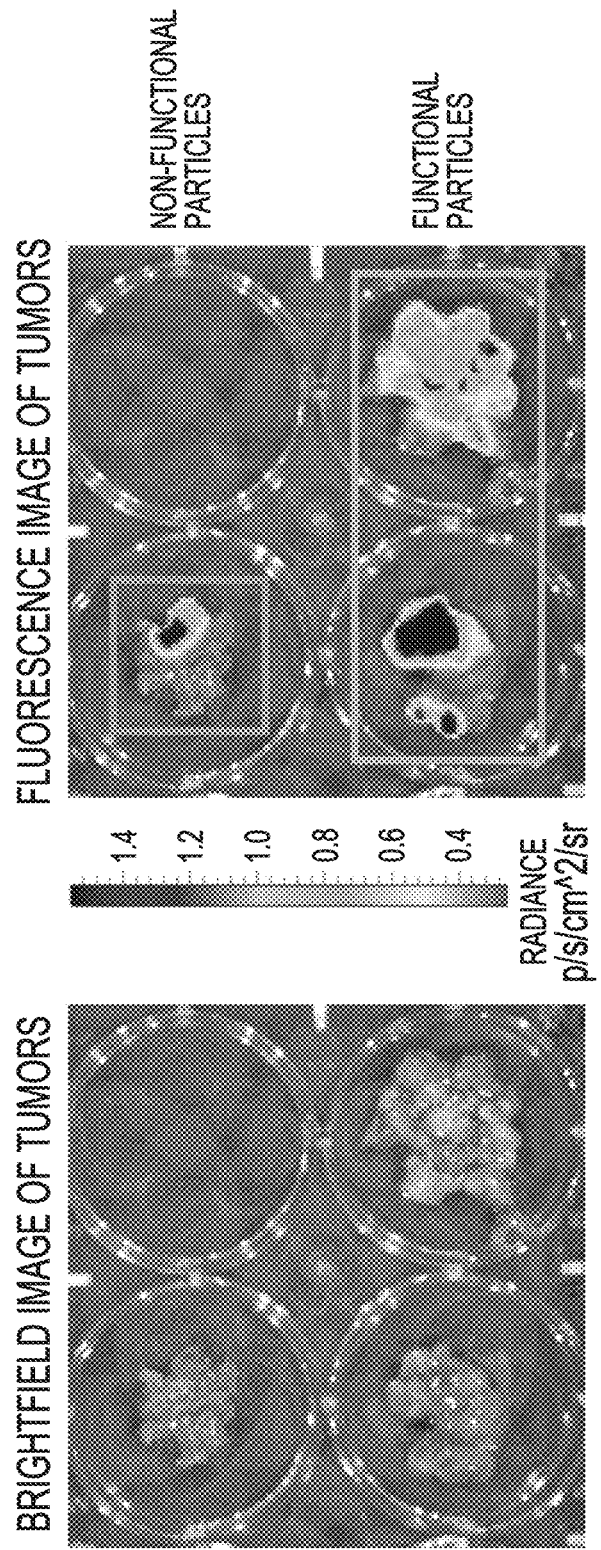
FIG. 10 provides a representation of differences in fluorescence where CFANs (i.e. 'Functional Particles') display brighter fluorescence in tumor tissue than NFNs (i.e. 'Nonfunctional Particles').

Increased Accumulation of Functional Nanoparticles in *Salmonella*-Infected Tumors in Mouse Model The bacteria-nanoparticle system was tested in mice to demonstrate the functionality of this technology in vivo. Accumulation of CFANs in bacteria-infected tumors was measured and compared to a control group consisting of NFNs. Briefly, 8-12-week-old C57BL6j male mice were injected with $1 \times 10^6$ MC38 cells in their right hind flank. Tumors were grown to ~500 mm³ before bacterial injection. *Salmonella*, VNP20009 specifically, used in this example were not arabinose-responsive and did not express GFP (see Example 8). *Salmonella* ($2\times10^7$ cfu) was injected intratumorally and allowed to proliferate for 48 hrs. Following this incubation period, approximately 200 uL of 2.5 mg/mL of nanoparticles in sterile PBS was administered intravenously via tail vein. Note that an additional filtration step was added to nanoparticle preparation to ensure sterility. After 4 hrs, mice were sacrificed, and the tumor was extracted. The tumor was cut in half: one half was used for IHC and the other for measuring the accumulation of nanoparticles in tumor tissue via fluorescence. The samples used for nanoparticle accumulation measurements were finely diced with a razor blade and placed in a 6-well plate. IVIS was used to measure fluorescence. Ex/em spectra was taken in the range from 600-740 nm. Live Imaging Software was used to perform spectral unmixing and quantify fluorescence values. Nanoparticle accumulation was determined by normalizing spectrally unmixed fluorescence values against the mass of each individual tumor tissue imaged and volume of nanoparticle suspension injected. Surprisingly, a 2.1-fold increase in particle accumulation was experienced with CFANs compared to NFNs. The results demonstrate that the proposed technology provides significant accumulation of nanoparticles in tumors compared to control systems that do not specifically target bacteria. A representation of differences in fluorescence can be seen in FIG. 10 where CFANs (i.e. 'Functional Particles') display brighter fluorescence in tumor tissue than NFNs (i.e. 'Non-functional Particles').

BIBLIOGRAPHY

R. Singh, S. Patil, N. Sing, S, Gupta. "Dual functionality nanobioconjugates targeting intracellular bacteria in cancer cells with enhanced antimicrobial activity." Scientific Reports. December 2017.

All publications, nucleotide and amino acid sequence identified by their accession nos., patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The specific methods and compositions described herein are representative of preferred embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acid or polypeptide preparations), and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

What is claimed is:

1. A method to target tumor-associated bacterial beacon cells in tumors of a subject comprising:
   i) first administering to the subject *Salmonella* bacterial beacon cells that colonize tumors, and
   ii) second administering to the subject nanoparticles having a payload and a functionable group that targets the colonized beacon cells of i).

2. A method to treat cancer in a subject in need thereof comprising:
   i) first administering to the subject *Salmonella* bacterial beacon cells that colonize tumors, and
   ii) second administering to the subject nanoparticles having a payload and a functionable group that targets the colonized beacon cells of i).

3. The method of claim 1, wherein at least one of the functional groups is an antibody.

4. The method of claim 1, wherein the payload or the nanoparticle comprises at least one of paclitaxel, albumin-based nanoparticle and paclitaxel, liposomal nanoparticle and doxorubicin, erlotinib, gefitinib, polymxin B, polymxin E, rituximab, bortezomib, rucaparib, sorafenib, liposomal nanoparticle and daunorubicin and cytarabine, liposomal doxorubicin, pegylated-liposomal nanoparticle formulation of doxorubicin, polymeric NP micelle formulation of paclitaxel or pegaspargase.

5. The method of claim 1, wherein the *Salmonella* is an attenuated strain of *Salmonella*.

6. The method of claim 5, wherein the attenuated strain of *Salmonella* is VNP20009.

7. The method of claim 1, wherein the *Salmonella* is a strain of *Salmonella Typhimurium*.

8. The method of claim 7, wherein the strain of *Salmonella Typhimurium* is an attenuated strain of *Salmonella Typhimurium*.

9. The method of claim 1, wherein the bacteria occupy tumor tissue entirely or partially extracellular.

10. The method of claim 2, wherein the bacteria occupy tumor tissue entirely or partially intracellular.

11. The method of claim 1, wherein the nanoparticle comprises or is formed of organic substances or inorganic substances.

12. The method of claim 11, wherein the substances comprise polymers, proteins, gold, silver, alumina, titania, and/or silica.

13. The method of claim 4, wherein the payload is paclitaxel.

14. The method of claim 1, wherein the nanoparticle is an albumin nanoparticle.

15. The method of claim 1, wherein the functional group is an antibody which targets *Salmonella*.

16. The method of claim 1, wherein the bacteria are attenuated *Salmonella*, the nanoparticle is an albumin nanoparticle and the functional group is an antibody which targets *Salmonella*.

17. The method of claim 1, wherein the payload is a cancer treatment.

* * * * *